US008173983B1

(12) United States Patent
Sahadevan

(10) Patent No.: US 8,173,983 B1
(45) Date of Patent: May 8, 2012

(54) ALL FIELD SIMULTANEOUS RADIATION THERAPY

(76) Inventor: Velayudhan Sahadevan, Beckley, WV (US)

( * ) Notice: Subject to any disclaimer, the term of this patent is extended or adjusted under 35 U.S.C. 154(b) by 24 days.

(21) Appl. No.: 12/655,825

(22) Filed: Jan. 7, 2010

(51) Int. Cl.
*A61N 5/10* (2006.01)
(52) U.S. Cl. ............... 250/494.1; 250/492.1; 250/492.3; 250/341.7; 378/64; 378/65; 600/427; 600/9
(58) Field of Classification Search ............... 250/341.7, 250/492.1, 492.3, 494.1; 378/64, 65; 600/9, 600/427
See application file for complete search history.

(56) References Cited

U.S. PATENT DOCUMENTS

| | | | |
|---|---|---|---|
| 3,752,989 A | 8/1973 | Motz et al. | |
| 4,321,208 A | 3/1982 | Sahadevan | |
| 4,455,277 A * | 6/1984 | Schlitt | 376/103 |
| 4,726,046 A | 2/1988 | Nunan | |
| 6,687,333 B2 * | 2/2004 | Carroll et al. | 378/119 |
| 7,027,553 B2 | 4/2006 | Dunham | |
| 7,366,279 B2 | 4/2008 | Edie et al. | |
| 7,391,850 B2 | 6/2008 | Kaertner et al. | |
| 7,486,984 B2 * | 2/2009 | Carroll | 600/436 |
| 7,636,417 B2 | 12/2009 | Bjorkholm | |
| 2006/0106301 A1 * | 5/2006 | Kats | 600/415 |
| 2006/0222147 A1 * | 10/2006 | Filkins et al. | 378/119 |

OTHER PUBLICATIONS

Sahadevan V. U.S. Appl. No. 11/998,063, filed Nov. 27, 2007 and its U.S. Appl. No. 60/872,117 of Nov. 30, 2006; Lethal and Sublethal Damage.
Hall E.J., Hyperthermia, Cellular Response to Heat, in Radiobiology for the Radiologist, Hall E. J. (Ed) fifth ed., p. 497-499, Lippencott Williams & Wilkins, 2000, Philadel.
Hall E.J., Hyperthermia, The Interaction Between Heat and Radiation, in Radiobiology for the Radiologist, Hall E. J. (Ed)., p. 508-510, fifth ed. Lippencott Williams & Willia.

(Continued)

*Primary Examiner* — Robert Kim
*Assistant Examiner* — Michael Logie

(57) ABSTRACT

This invention describes a system for generating multiple simultaneous tunable electron and photon beams and monochromatic x-rays for all field simultaneous radiation therapy (AFSRT), tumor specific AFSRT and screening for concealed elements worn on to the body or contained in a container. Inverse Compton scattering renders variable energy spent electron and tunable monochromatic x-rays. It's spent electron beam is reused for radiation with electron beam or to generate photon beam. Tumor specific radiation with Auger transformation radiation is facilitated by exposing high affinity tumor bound heavy elements with external monochromatic x-rays. Heavy elements like directly iodinated steroid molecule that has high affinity binding to estrogen receptor in breast cancer and to iodinated testosterone in prostate cancer or with directly implanted nanoparticles into the tumor are exposed with tuned external monochromatic x-rays for tumor specific radiation therapy. Likewise, screening element's atom's k, l, m, n shell specific Auger transformation radiation generated by its exposure to external monochromatic x-rays is used to screen for concealed objects. Multiple beam segments from a beam storage ring or from octagonal beam lines are simultaneously switched on for simultaneous radiation with multiple beams. The beam on time to expose a tumor or an object is only a few seconds. It also facilitates breathing synchronized radiation therapy. The intensity modulated radiation therapy (IMRT) and intensity modulated screening for concealed objects (IMSFCO) is rendered by varying beam intensities of multiple simultaneous beams. The isocentric additive high dose rate from simultaneously converging multiple beams, the concomitant hyperthermia and chemotherapy and tumor specific radiation therapy and the AFSRT's very low radiation to the normal tissue all are used to treat a tumor with lower radiation dose and to treat a radioresistant and multiple times recurrent tumors that heave no other alternative treatments.

19 Claims, 17 Drawing Sheets

OTHER PUBLICATIONS

Hall E.J., Hyperthermia, Heat and Chemotherapeutic Agents in Radiobiology for the Radiologist, Hall E. J. (Ed)., p. 510-512, fifth ed. Lippencott Williams & Wilkins, 2000, P.

Khan F. M. : Electron Beam Therapy, X-Ray Contamination, in the Physics of Radiation Therapy, p. 317-318 Khan, F. M.(ed), 2003, Lippencott Williams & Wilkins, Philadelphia.

Khan F. M. : Electron Beam Therapy, Beam Collimation, in the Physics of Radiation Therapy, p. 312 Khan, F. M.(ed), 2003, Lippencott Williams & Wilkins, Philadelphia.

Khan F. M. : Electron Beam Therapy, Effects of Blocking on Dose Rate , in the Physics of Radiation Therapy, p. 332-333, Khan, F. M.(ed), 2003, Lippencott Williams & Wilkin.

Khan F. M. : Electron Beam Therapy, Electron Arc Therapy, in the Physics of Radiation Therapy, p. 337 Khan, F. M.(ed), 2003, Lippencott Williams & Wilkins, Philadelphia.

Khan F. M. : Electron Beam Therapy, Measurement of Transmission Curves, in the Physics of Radiation Therapy, p. 331-332 Khan, F. M.(ed), 2003, Lippencott Williams & Wilkins. P.

Khan F. M. : Electron Beam Therapy, Characteristics of Clinical Electron Beams, in the Physics of Radiation Therapy, p. 307 Khan, F. M.(ed), 2003, Lippencott Williams & Willia.

Pradhan A. K. et al., Resonant X-ray Enhancement of the Auger Effect in High-Z Atoms, Molecules, and Nanoparticles: Potential Biomedical Applications: J. Phys. Chem. A 2009.

Hall E.J., Carcinogenesis: The Human Experience, in Radiobiology for the Radiologist, Hall E. J. (Ed) fifth ed. p. 145-149, Lippencott Williams & Wilkins, 2000, Philadelphia.

Smith-Bindman, et. al., Radiation Dose Associated With Common Computed Tomography Examinations and the Associated Lifetime Attributable Risk of Cancer: Arch Intern Med/Nol.

Xiaowei Yang et al., Synergistic Activation of Functional Estrogen Receptor (ER)-α by DNA Methyltransferase and Histone Deacetylase Inhibition in Human ER-α—negative Breast.

Sahadevan. V., U.S. Appl. No. 11,974,876, filed Apr. 5, 2007 and its U.S. Appl. No. 60/790,192, filed Apr. 6, 2006; Multiple Med.

Dunham B. M., Systems and Methods for Generating Images by Using Monochromatic X-Rays: Patent US 7,027,553, Apr. 11, 2006.

Khan F. M. :Characteristic X-rays, in the Physics of Radiation Therapy, p. 34-35 Khan, F. M.(ed), 2003, Lippencott Williams & Wilkins, Philadelphia.

Sahadevan V. and Sahadevan V. C., Estrogen Contents of Estrogen Receptor Positive and Negative Breast Cancer: Unpublished data, 1980.

Montenegro M. et el., Monte Carlo Simulation and Atomic Calculations for Auger Process in Biomedical Nanotheranostics: J. Phys. Chem., A 2009, 113, 12364-12369.

Hall E.J., Linear Energy Transfer: in Radiobiology for the Radiologist, Hall E. J. (Ed)., p. 113-114, fifth ed. Lippencott Williams & Wilkins, 2000, Philadelphia.

Khan F. M. : Treatment Planning I: Isodose Distributions, B. Rotation Therapy, Example, in the Physics of Radiation Therapy, p. 216-217 Khan, F. M.(ed), 2003, Lippencott Wil.

\* cited by examiner

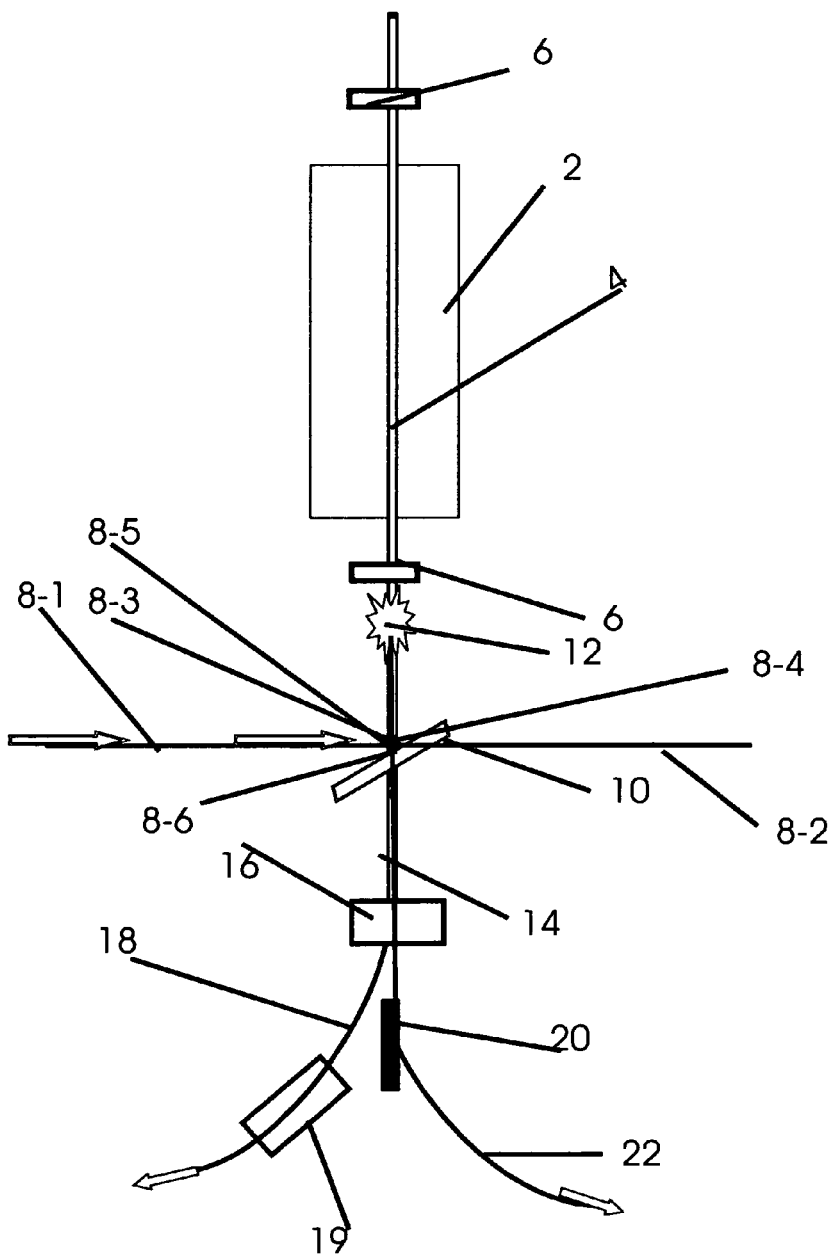

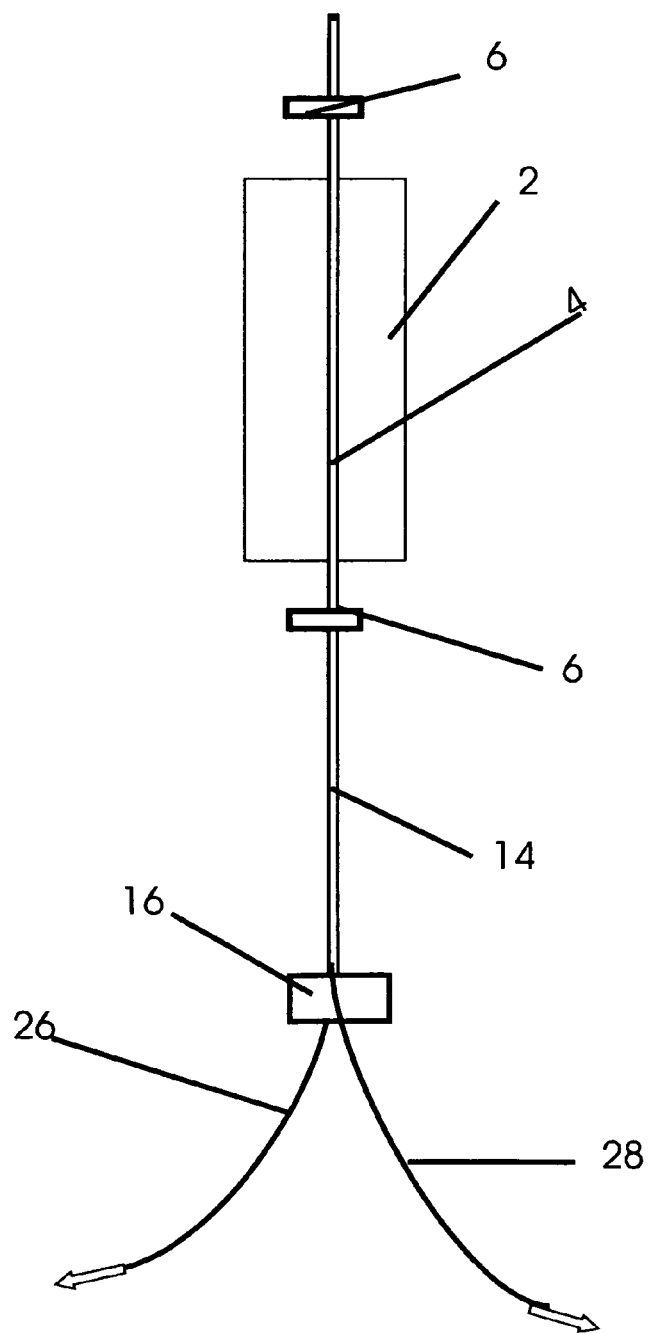

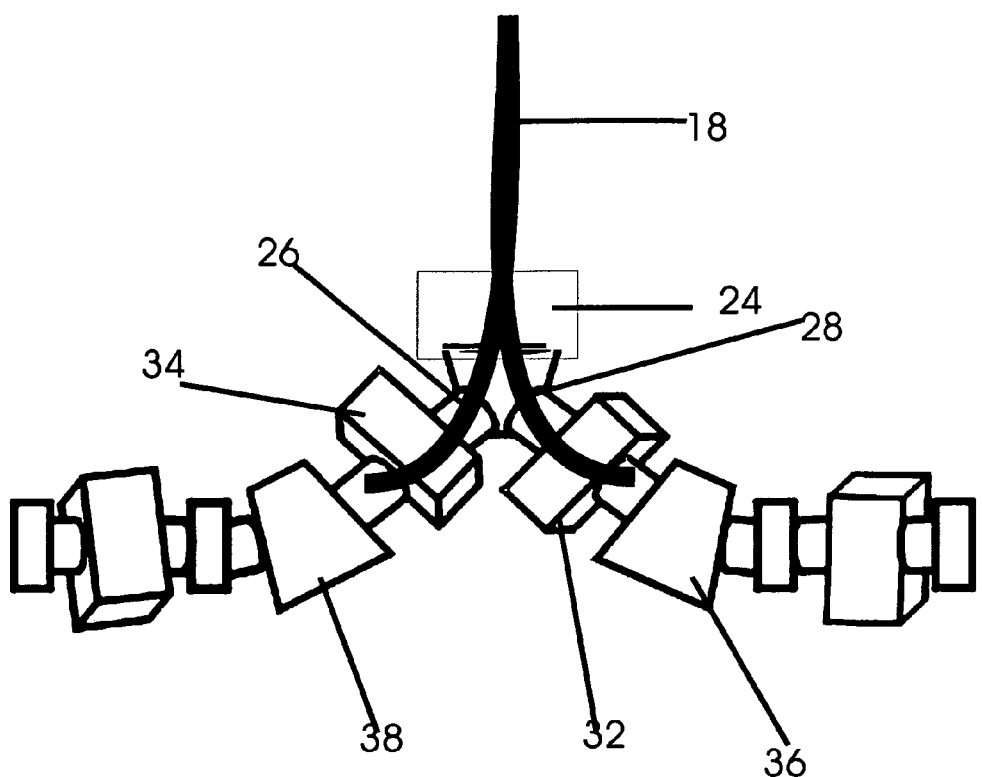

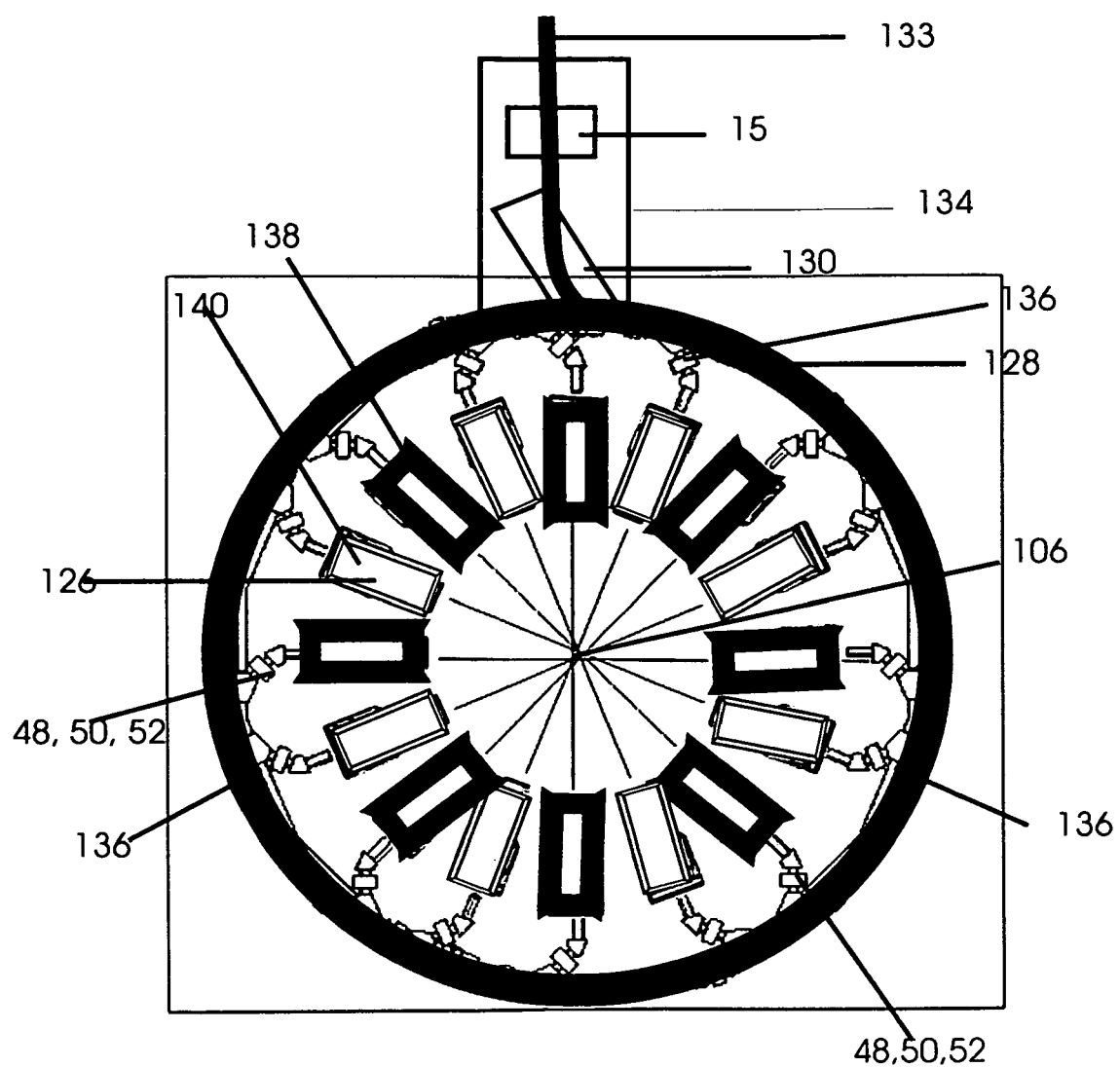

ALL FIELD SIMULTANEOUS RADIATION THERAPY

CROSS-REFERENCE TO RELATED APPLICATIONS

Table of Contents:

| Page # | Line # | Title |
|---|---|---|
| 1 | 4 | Cross reference |
| 1 | 25 | Background |
| 2 | 23 | Electron beam Radiation Therapy |
| 3 | 16 | Inverse Compton Scattering (ICS), Monochromatic X-Ray Imaging |
| 4 | 22 | Inverse Compton scattering x Ray's Electron Beam for Radiation Therapy |
| 5 | 21 | All Field Simultaneous Radiation Therapy Combined with Monochromatic X-Ray Imaging |
| 6 | 21 | Few Seconds Beam on Time All Field Simultaneous Radiation Therapy |
| 9 | 17 | Radiation Therapy of "Radioresistant" and Recurrent Tumors with Low Dose to Normal Tissue |
| 11 | 17 | Comparison of All Field Simultaneous Radiation Therapy with Brachytherapy |
| 12 | 19 | All Field Simultaneous Radiation Therapy and Intensity Modulated Conformal Radiation Therapy |
| 13 | 8 | The linear energy transfer (LET) Concept in All Field Simultaneous Radiation Therapy |
| 15 | 4 | All Field Simultaneous Radiation Therapy and Its Interaction with Heat, and Chemotherapy |
| 16 | 23 | Diagnostic Bremsstrahlung X-Ray and Radiation Carcinogenesis |
| 17 | 17 | Advantages of Radiological Imaging with Monochromatic X-Rays |
| 18 | 17 | Iodinated Steroids and Iodine k, l, m, n Shell Characteristic Photon and Auger Electron for Imaging and Radiation Therapy |
| 19 | 1 | Tumor Specific K-Shell Electron Radiation Therapy and Imaging of Estrogen Receptor Positive and Negative Breast and Testosterone Receptor Positive and Negative Prostate Cancer |
| 21 | 19 | Whole body Screening for Concealed Objects by Computerized Tomography with Multiple Simultaneous Monochromatic X-Ray and Spent Electron Beams |
| 23 | 1 | Brief Summary of the Invention |
| 26 | 7 | Brief description of the drawings |
| 28 | 22 | Reference Numerals |
| 33 | 4 | Description of the Preferred Embodiments |
| 33 | 7 | FIG. IA, Inverse Compton scattering |
| 34 | 9 | FIG. 1B, electron switched in to two beams |
| 34 | 18 | FIG. 1C, separated electron beamlets |
| 35 | 1 | FIG. 1D, collilinear electron beam and the monochromatic x-ray beam |
| 35 | 7 | FIG. 2, two beamlets steered into beam lines |
| 35 | 13 | FIG. 3, extracted beam from beam line and taken to target or to treatment head and to imaging head and other portion continues |
| 36 | 1 | FIG. 4 extracted beam from beam line and taken to target or to treatment head and to imaging head and other portion continues |
| 37 | 1 | FIG. 5, single octagonal beam line, 7 treatment heads, beam switching magnets |
| 37 | 16 | FIG. 6, two octagonal beam lines with 16 treatment heads, beam switching magnets |
| 39 | 1 | FIG. 7, treatment heads 5 degree tilt, stationary circumferential collimated detectors outside the beam lines |
| 40 | 8 | FIG. 8, exposure of the detectors by exiting attenuated multiple simultaneous beams from tilted treatment heads |
| 40 | 15 | FIG. 9, treatment heads with electron cone |
| 45 | 1 | FIG. 10A, beam storage ring |
| 50 | 11 | FIG. 10B, beam switching from the storage ring |
| 50 | 25 | FIG. 10C, switched beam guidance towards treatment head and imaging head |
| 52 | 1 | FIG. 11A, U.S. Pat. No. 7,027,553 - GE |
| 52 | 23 | FIG. 11B, U.S. Pat. No. 7,027,553 - GE modified |
| 54 | 5 | Methods of Operation |
| 56 | 18 | Screening for Concealed Elements Worn on to the Body or Contained in a Container by Whole body Computerized Tomography and Radiology with Monochromatic High-flux Short-pulse X-Rays AND Spent Electron Beam |
| 66 | 1 | What is claimed is: |
| 74 | 1 | Abstract |
| 75 | 1 | References |
| 78 | 11 | Table of contents |
|  |  | FIGS. |
| 82 |  | FIG. 1A |
| 83 |  | FIG. 1B |
| 84 |  | FIG. 1C |
| 85 |  | FIG. 1D |
| 86 |  | FIG. 2 |
| 87 |  | FIG. 3 |
| 88 |  | FIG. 4 |
| 89 |  | FIG. 5 |
| 90 |  | FIG. 6 |
| 91 |  | FIG. 7 |
| 92 |  | FIG. 8 |
| 93 |  | FIG. 9 |
| 94 |  | FIG. 10A |
| 95 |  | FIG. 10B |
| 96 |  | FIG. 10C |
| 97 |  | FIG. 11A |
| 98 |  | FIG. 11B |

This Application claims the benefit of provisional and non-provisional patent Applications, 60/790,192, filed on Apr. 6, 2006 and Ser. No. 11/784,398 filed on Apr. 5, 2007 and its continuation application Ser. No. 11/974,876 filed on Oct. 15, 2007, "Multiple medical accelerators and kV-CT incorporated radiation therapy device and semi-automated custom reshapeable blocks for all field synchronous image guided 3-D conformal-intensity modulated radiation therapy"; Provisional and non-provisional Patent Applications 60/872,117, filed on Nov. 30, 2006 and Ser. No. 11/998,063 filed on Nov. 27, 2007 "Lethal and Sublethal Damage Repair Inhibiting Image Guided Simultaneous All Field Divergent and Pencil Beam Photon and Electron Radiation Therapy and Radiosurgery"; Provisional and non-provisional Patent Applications 60/927,622, filed on May 3, 2007 and 12/151,014 filed on May 3, 2008 "Single session interactive image guided simulation, field shaping, treatment planning and ultra short duration, super-high biological dose rate all field simultaneous or sequential radiation therapy and radiosurgery"; and none-provisional patent application Ser. No. 12/459,120 filed on Jun. 25, 2009 "Few Seconds Beam-on Time Breathing Synchronized Image Guided All Fields Simultaneous Radiation Therapy Combined with Hyperthermia.

Federally Sponsored Research: None; Sequence Listing: Table of Contents attached

BACKGROUND OF THE INVENTION

The advantages of few seconds duration all filed simultaneous radiation therapy (AFSRT) with super high combined dose rate at isocenter is described in above cross-referenced non-provisional and provisional patent applications and disclosure. The AFSRT overcomes the disadvantages associated with lower daily radiation dose.

The isocentric super high dose rate of all field simultaneous radiation therapy (AFSRT) is the combined dose rate of all converging simultaneous beams at the isocenter (1). Its ($3D^2$ cell kill is much higher than in conventional radiation therapy that is delivered by subfractionated daily-fractionated radiation therapy. Here, the daily subfractionated radiation therapy is referred to as the daily-fractionated radiation therapy that is further subfractionated by treating each field sequentially. Such daily fractionated treatment is interrupted by the time required for sequential setup of treatment fields and then switching the beam on for the treatment. When a tumor at isocenter is treated by the method of AFSRT, the $D_{max}$ dose to normal tissue depends on the number of simultaneous beams; as described below, it is very much reduced.

The production of monochromatic, high-flux, short-pulse x-rays with the interaction of electron beam and laser photon beam uses high energy electron beam, in the range of about 25-44 and higher MeV. After the electron-laser photon beam interaction, the high energy electron beam is dumped as a waste product (2, 3). The electron beam source can be from a conventional linear accelerator (2), a superconducting linear accelerator (3) or any other high energy electron beam generating accelerators like the Betatron, Microtron, Racetrack Microtron or any other high energy electron beam generators. In this invention, such high energy electron beam is used for direct electron/photon beam radiation therapy. The monochromatic x-ray pulse generated by the interaction of electron and laser photon beams is used for imaging combined with radiation therapy and tumor specific radiation.

Electron Beam Radiation Therapy

External beam radiation therapy is mostly delivered by high energy photon beam. An alternative method of radiation therapy with high energy electron would eliminate the about 45% exit dose contribution from the parallel opposing beam to the skin as in radiation therapy with photon beam. The electron beam do not generate contaminating direct neutron beam or by its interaction with a patient as by the photon beam. The contaminating x-ray beam of the high energy electron beam could reach the opposite side of a treatment field but it is generally very low as compared to the photon beam's exit dose. Furthermore, the filtered contaminating x-ray at the tail end of the electron beam is superior to the monochromatic filtered low energy x-rays that are also used for phase contrast imaging. The 90 and 80% of the electron beam is approximately E/3.2 and E/2.8. Hence the 30 MeV electron beam's useful treatment depth at 90 and 80% is about 10 and 12.5 cm. It is a sufficient depth dose for routine radiation therapy. Taking the loss of electron energy at a rate of about 2 MeV/cm of water or soft tissue, the 30 MeV electron beam's range is about 15 cm. Hence the 30 MeV electron beam's dose contribution to the opposite side of an average person with 20 cm circumference is negligent except for its small amount of x-ray contamination.

Inverse Compton Scattering (ICS), Monochromatic X-Ray Imaging

Interaction of electron beam with laser beam is used to generate short pulse monoenergetic x-ray beam (2, 3). Such inverse Compton scattering monoenergetic x-ray offers numerous advantages to study the biological events that takes place immediately after radiation. It offers the opportunity to facilitate monochromatic x-ray image guided radiation therapy. In phase contrast imaging of tissue with short pulse monoenergetic x-rays, the perturbaration of x-rays by the component of the cellular elements is visualized. When imaging is by bremsstrahlung x-rays, the x-ray is absorbed by the tissue. The phase contrast imaging minimizes the x-ray dose to tissue than the conventional methods of imaging with bremsstrahlung x-rays. It is also suited for phase contrast imaging during and or immediately after radiation therapy. The few seconds duration all field simultaneous radiation therapy with isocentric super high dose rate and tumor specific k-edge radiation will cause much more DNA damage and molecular level reactions. The combined radiation therapy and molecular imaging by phase contrast is an entirely newer method of radiation therapy of cancer. It offers unsurpassed opportunities like in vivo imaging of protein constituents in tissue that is radiated with super high dose rate radiation. It allows to investigate the radiated tissue's magnetic scattering, time dependent radiation induced $^-OH$ ion migration to DNA and DNA double strand breaks, the effects of hyperthermia combined with radiation therapy and formation of receptor-ligand complexes in tumor tissue like that of hormones and chemotherapeutic agents. It also offers many other investigational opportunities including spectroscopic analysis of structural differences in proteins in normal and tumor cells as well as the structural genomics of the normal and cancer cells. They would help to correlate and predict the outcome of a treatment modality at molecular level, especially of the potential tumor cure, recurrence and metastasis.

Recently, less expensive, compact monochromatic high brilliance x-ray production sources are described (2, 3). In such high brilliance x-ray source generation, high energy electron is made to interact with laser photon beam. This electron-laser interaction generates inverse Compton x-ray which is used for phase contrast imaging.

Inverse Compton scattering X-Ray's Electron Beam for Radiation Therapy

In inverse Compton scattering x-ray generation as in U.S. Pat. No. 6,687,333 B2 by Carroll F. E et al (2), in U.S. Pat. No. 7,391,850 by Kaertner et al (3) and in U.S. Pat. No. 7,027,553 by Dunham B. M (22), after the electron—laser interaction, the spent high energy electron beam is "dumped" away as a waste product. In this invention, instead of dumping this spent electron beam, it is reused for either electron beam radiation therapy or for photon beam radiation therapy. Alternatively, after the monochromatic x-ray imaging, separate electron beams suitable for radiation therapy is generated in the accelerator unit that is used to generate the electron beam. By varying the wave length of the laser or the energy of the electron beam, different energy, tunable monochromatic x-ray is obtained.

For all field simultaneous radiation therapy, the spent electron beam of the inverse Compton reaction is deflected into circular beam lines that are equipped with multiple treatment heads. The electron beam energy used for generating monochromatic, high pulse x-ray ranges from 25-44 MeV and higher (2,3, and 22). This electron beam is used for high energy electron beam radiation or to generate high energy photon beam for photon beam radiation. Alternatively, separate lower energy electron beam is generated in the accelerator for lower energy radiation therapy. In this instance the electron accelerator operates in multiple energy modes. The high flux short pulse monochromatic x-rays generated by the interaction of electron beam and the laser beam is deflected for phase contrast imaging and the electron beam that is deflected into the beam line is used for radiation therapy.

All Field Simultaneous Radiation Therapy Combined with Monochromatic X-Ray Imaging The method of generating monochromatic high flux, short pulse x-ray beam is described in U.S. Pat. No. 6,687,333 B2 by Carroll F. E et al (2), in U.S. Pat. No. 7,391,850 by Kaertner et al (3) and in U.S. Pat. No. 7,027,553 by Dunham B. M (22). The high flux, short wave x-ray is deflected into a collimated imaging system for imaging. Imaging with monochromatic x-ray renders 100-100 times superior image quality with much less radiation to the target tissue (2). The electron is deflected into a beam line for all field simultaneous radiation therapy. It offers simultaneous imaging while radiation therapy is rendered. Alternatively, after the phase contrast imaging the high energy electron beam is dumped as a waste and for radiation therapy, lower energy, say 6 or 10 MeV is generated in the accelerator as separate beam and deflected into the beam line for radiation therapy. After or even during the radiation therapy, phase contrast imaging is used to analyze radiation induced reactions in the cell. It allows imaging of cellular level events during or after radiation. Such elaborate image guided radiation therapy is not feasible with present image guided radiation therapy.

The electron beam that is deflected into the beam line is split into two at each station where a treatment head is located. One of such split beam is bent towards treatment head. The other beam is bent towards the next treatment head where it is spit into two again, one is bent towards the next treatment head and the other is deflected towards the next treatment head. This process of splitting the beam and bending one beam towards a treatment head and another beam towards the next station where the next treatment head is located is repeated until all the simultaneous beams are generated for all filed simultaneous radiation therapy.

Few Seconds Beam on Time All Field Simultaneous Radiation Therapy

The beam on time for all field simultaneous radiation therapy with multiple simultaneous beams is very short. The beam on time is 40 seconds if it were a four field simultaneous radio surgical dose were 800 cGy. This beam on time is progressively decreased as the number of simultaneous beams are increased; if it were a 8, 16 or 32 simultaneous beams system, then the beam on time to deliver 800 cGy will be decreased to 20, 10 and 5 seconds respectively. Because of this system's super high dose rate associated improved RBE, the single dose of 800 cGy might be equivalent to about 1,000 cGy or higher. A patient can be instructed to hold breathing for 5-20 seconds. It enables breathing synchronized radiosurgery. If it were a medical accelerator system with four simultaneous beams, the beam on time to deliver 800 cGy single doses would be 40 seconds. It is a longer time for a patient to hold the breathing. In this instance, breathing synchronized two fractions of 400 cGy are delivered, each fraction's beam on time lasting 20 seconds. The beam on time for conventional 200 cGy daily fractionated radiation therapy is 5 seconds. It is rendered as breathing synchronized radiation therapy.

If the single beams dose rate were 200 cGy and isocentric depth 10 cm below the skin and if the average TMR were 0.746, $S_c$ 0.98, $S_p$ 0.99 then the $D_{iso}=D_0$ 200 cGy×0.746×0.98×0.99 which is 144.8 cGy. (29). Likewise, if the single beams dose rate were increased to 400 cGy and isocentric depth 10 cm below the skin and if the average TMR, $S_c$ and $S_p$ were same as above, then the $D_{iso}=D_0$ 400 cGy×0.746×0.98×0.99 which is 289.5 cGy. If the number of simultaneous beams were 2, 4, 8, 16 or 32, then the isocentric additive (biological dose rates) for this AFSRT system is 2×289.5=579 cGy/min, 4×289.5=1,158 cGy/min, 8×289.5=2,316 cGy/min, 16×289.5=4,632 cGy/min and 32×289.5=9,264 cGy/min (1). If 800 cGy $D_{iso}$ were given by 2, 4, 8, 16 or 32 simultaneous beams and each beams having 400 cGy/min dose rates, then each beams delivers 400, 200, 100, 50 or 25 cGy at the isocenter. It is proportional to the isocentric dose 800 cGy divided by the number of beams. Alternatively it can be calculated by dividing each beam's contribution divided by each beam's $D_{iso}$ dose rate of 289.5 cGy. If there are two simultaneous beams, then the treatment time to deliver 800 cGy at the isocenter is (800/2)/289.5, which is 1.3817 min or 82.9 seconds. In this instance, the MU set up for each beam is $D_0$ dose rate per min 400×1.3817, which is 552.677, or 553. Likewise, if there are four simultaneous beams, then the treatment time is reduced to (800/4)/289.5, which is 0.6908 min or 41.45 seconds. In this instance, the MU set up for each beam is $D_0$ dose rate per min 400×0.6908, which is 276. Similarly, if it were eight simultaneous beams, then the treatment time is reduced to (800/8)/289.5, which is 0.3454 min or 20.7254 seconds. In this instance, the MU set up for each beam is machine dose rate per min 400×0.3454, which is 138. Likewise, if it were sixteen simultaneous beams, then the treatment time is reduced to (800/16)/289.5, which is 0.1727 min or 10.362 seconds. In this instance, the MU set up for each beam is machine dose rate per min 400×0.1727, which is 69. Similarly, if it were 32 simultaneous beams, then the treatment time is reduced to (800/32)/279, which is 0.0864 min or 5.1813 seconds. In this instance, the MU set up for each beam is machine dose rate per min 400×0.0896, which is 34.54. By increasing the number of beams from different angles, the $D_0$ dose is decreased while the isocentric additive dose rate is maintained as the same. The decrease in individual beam's dose contribution at the isocenter is proportional to the number of simultaneous beams.

Alternatively, individual beam's beam on time can be calculated from the isocentric total dose $D_{iso-T}$ divided by total additive $D_0$ dose rate, $D_{0-T}$. The MU setup for each of the simultaneous beam is then each individual beam's dose rate $D_0$ x beam on time. If the individual beam's dose rate were 400 cGy/min and the treatment parameters the same as above, then the individual beam's $D_{iso}$ dose rate is 289.5 cGy/min. The tumor dose is kept as the same before, 800 cGy. If the number of simultaneous beams were 2, 4, 8, 16 or 32, then the total additive dose rates, $D_{0-T}$ are 400×2=800, 400×4=1,600, 400×8=3,200, 400×16=6,400 and 400×31=12,800 cGy. These 2, 4, 8, 16 or 32 simultaneous beams's total additive dose rate $D_{iso-T}$ (biological dose rates) is 2×289.5=579, 4×289.5=1,158, 8×289.5=2,316, 16×289.5=4,632 and 32×289.5=9,264 cGy/min. Then the beam on time to deliver 800 cGy at the isocenter for 2, 4, 8, 16 or 32 simultaneous beams is 800/579, 1,158, 2,316, 4,632 or 9,264 cGy. It is 1.3817, 0.6908, 0.3454, 0.1727 and 0.0864 min respectively. Since the individual beam's dose rate is 400 cGy/min, when 2, 4, 8, 16 or 32 simultaneous beams are used, the individual beam's MU set up is 400×1.3817=553, 400×0.6908=276, 400×0.3454=138, 400×0.1727=69 or 400×0.0864=35. It is the same as in method of MU calculation for two beams.

For parallel opposed photon beam treatment method, the maximum dose to the normal tissue, $D_{max}$ is approximately $D_0$×45% of the $D_0$ dose from the opposite beam. When 800 cGy tumor dose is delivered at the isocenter, the MU setup when the treatment is rendered with 2, 4, 8, 16, and 32 simultaneous beams are 553, 276, 138, 69 and 35. Hence, the $D_{max}$ dose for 2, 4, 8, 16 and 32 simultaneous beams are 553+249=802, 276+124=400, 138+62=200, 69+31=100, and 35+16=51 cGy. Thus by increasing the number of simultaneous beams, the dose to the normal tissue D. is decreased.

Radiation Therapy of "Radioresistant" and Recurrent Tumors with Low Dose to Normal Tissue Radiation therapy and radiosurgery with low maximum dose to normal tissue is better tolerated. It causes much less damage to normal tissue, the most limiting factor in radiation therapy. As the number of simultaneous beams is increased the dose to normal tissue is decreased. When the radiosurgical tumor dose is 800 cGy and the number of simultaneous beams is 8, 16 or 32 then the maximum dose to normal tissue are 200, 100 or 51 cGy. It includes the 45% dose contribution from the exiting opposing beam. Such lower dose to normal tissue is better tolerated. It facilitates radiosurgery of tumors that are very close to critical organs. In this instance, higher tumor dose is delivered by the method of simultaneous multiple beams radiation therapy while keeping the dose to normal tissue low. Because of the normal tissue intolerance to very high dose radiation, the "radio-resistant" tumors are generally treated with insufficient total tumor dose. Hence the so called "radioresistant" tumors like the melanoma are treated with lower non-curate total dose. The method of all filed simultaneous radiation to a tumor with lower dose to normal tissue and higher curative dose to tumor helps to overcome the "radioresistance" of tumors like melanoma.

Because of the lower tolerance of radiation by the normal tissue when a recurrent tumor is treated, the re-treatment of a tumor by radiation causes more complications. Because of the previous radiation, the normal tissue tolerance to radiation is low. Hence the recurrent tumors that had initial radiation therapy cannot tolerate repeat second, third or even higher retreatments. On the other hand, radiation therapy with lower dose to normal tissue by the method of all field simultaneous radiation is tolerated by the normal tissue. Hence this method of radiation therapy with multiple simultaneous beams offers the opportunity to treat recurrent and "radioresistant" tumors by radiosurgery more effectively. By this method of multiple simultaneous beams radiation therapy, the recurrent tumors that had initial radiation can be retreated for a second, third or even higher times. It opens an entirely new avenue for treating recurrent and "radioresistant" tumors that were thought as impossible before.

The same method of treating tumors by low maximum dose to normal tissue is applicable when a tumor is treated by daily fractionated radiation. If the number of simultaneous beams is 2, 4, 8, 16 or 32 and each beam's $D_0$ dose rate 400 cGy, then the total additive dose rates, $D_{0-T}$ are 800, 1,600, 3,200, 6,400 and 12,800 cGy. These 2, 4, 8, 16 or 32 simultaneous beams' total additive dose rate $D_{iso-T}$ (biological dose rates) is 579, 1,158, 2,316, 4,632 and 9,264 cGy/min. As shown before, then the beam on time to deliver the conventional daily fractionated tumor dose of 180 cGy at the isocenter with 2, 4, 8, 16 or 32 simultaneous beams is 180/579, 1,158, 2,316, 4,632 or 9,264 cGy. It is 0.3109, 0.1554, 0.0777, 0.0389 and 0.0195 min respectively. Since the individual beam's dose rate is 400 cGy/min, when 2, 4, 8, 16 or 32 simultaneous beams are used, the individual beam's MU set up is 400×0.3109=124, 400× 0.1554=62, 400×0.0777=31, 400×0.0389=16 and 400×0.0195=8. Such low maximum dose to normal tissue is readily tolerated. It also makes higher total dose radiation therapy of tumors like melanoma that needs very high dose to cure and re-treatment of recurrent tumors that were previously treated by radiation more tolerable to normal tissue; the toxicity to normal tissue from such radiation is much reduced or even eliminated. Hence this method of treatment with multiple simultaneous beams offers the opportunity to treat "radioresistant" and recurrent tumors with radiation very effectively. It opens an entirely new avenue for control and or cure of "radioresistant" and recurrent tumors.

Comparison of All Field Simultaneous Radiation Therapy with Brachytherapy

The dose rate and LET are the major factors that determine the radiobiological effectiveness (RBE). The multiple simultaneous beams additive dose rate has some similarity with brachytherapy with multiple radioactive sources. Higher the number of radioactive sources used, higher the brachytherapy's additive dose rate. Hence, for brachytherapy dose calculations, the number of radioactive sources used determines its dose rate and the total dose needed to treat a tumor. For example, in brachytherapy the total dose at dose rate of 0.357 Gy/h (35.7 cGy/h) for 7 days is 6,000 cGy. Its equivalent dose at the dose rate of 0.64 Gy/h (64 cGy/h) for 7 days is 4,600 cGy. Likewise, in AFSRT, the dose rate is a function of the number of simultaneous beams and its additive super high dose rate which is designated as super high biological dose rate. This very high biological dose rate contributes the much improved radiobiological end results. Brachytherapy cannot achieve super high dose rate like the dose rate of multiple simultaneous external beams from linear accelerators. Even a single external beam from a medical accelerator has several hundred times more dose rate per minutes than the combined cGy/h dose rate of high dose rate (HDR) brachytherapy. The clinically useful super high dose rate of multiple simultaneous external beams cannot be reached by high dose rate brachytherapy or by the combined dose rate of Gamma Knife with several small $^{60}$Co sources. Hence the isocentric super high dose rate external photon beam radiation therapy cannot be compared with HDR brachytherapy or radiosurgery with Gamma Knife with an average dose rate of 145 cGy/min. Depending on the number of beams and individual beam's machine dose rate, its biological dose rate at isocenter varies. For a 10×10-cm field size, 10-cm depth, 100-cm isocenter distance, and machine dose rate of 400 cGy/min, the isocentric additive biological dose rates for 2, 4, 6, 8, 16 or 32 simultaneous beams of the AFSRT system is 579, 1,158, 1,737,2,316, 4,632 and 9,274 cGy/min respectively.

All Field Simultaneous Radiation Therapy and Intensity Modulated Conformal Radiation Therapy The AFSRT's multiple simultaneous high-energy photon and electron beam accelerators helps to produce conformal intensity modulated treatment as a single session treatment with simultaneous multiple beams that covers the entire treatment volume. Each of the isocentric simultaneous beam's intensity is modulated to suite the three-dimensional volume of the target. Such conformal intensity modulated simultaneous treatment of a target tumor as in the AFSRT is not feasible with the Gamma Knife or with the conventional single beam accelerator based radiosurgery. The radiobiological effectiveness of this new method of conformal treatment of a target volume with accelerator based simultaneous multiple beams with higher energy, higher dose rate and LET is much superior to that of radiosurgery with Gamma Knife or conventional linear accelerator based radiosurgery.

The linear energy transfer (LET) Concept in All Field Simultaneous Radiation Therapy The linear energy transfer (LET) values vary for different sources of high-energy radiation beams. The LET is subdivided into track average and energy average. In track average, the amount of energy deposited in equal lengths is averaged. In energy average, the length of the track that contains equal amount of energy is calculated. (28). For x-rays, both energy average and track average are similar. Both the track average and energy average for Cobalt-60 is 0.2 KeV/µ. Likewise, the track average and energy average for 250-kV x-rays is 2.0 KeV/µ, ten times higher than that for Co-60. Because of the lower LET of Cobalt-60 with 0.2 KeV/µ has about 10% less relative biological effectiveness (RBE) than that for 250 kV x-rays.

Unlike the x-ray beams, the proton beam's LET varies with energy. The 10 MeV proton has 4.7 KeV/µ energy averages while the energy average of 150 MeV proton is like that of $^{60}$Co, only 0.5 KeV/µ. Like the x-rays, both the energy and track average for proton is the same. Hence 150 MeV protons are less effective in cell kill than 250 kV x-rays. For neutrons the track and energy average vary. The 14 MeV neutron's track average is 12 KeV/μ but its energy average is 100 KeV/μ. Because of this very high-energy average, neutron is much more effective in cell kill.

A single 250-kV x-ray beam with 2.0 KeV/μ LET deposits its energy of 2.0 KeV/μ. when it passes through the radiating tissue. Let us say that this 250-kV x-ray source is placed at 0-degree. When it is used to radiate the tissue, it's beam deposits 2.0 KeV/μ to the tissue. If a second similar x-ray source is placed at the opposite side say at 180-degree as parallel opposed to the first source and when the x-ray beams from both sources are allowed to passes through the same tissue simultaneously as parallel opposed beams, then the converging beam's energy deposited in the target tissue could double. Now the total energy deposited in the target tissue could increase from 2 KeV/μ to 4.0 KeV/μ. If similar two simultaneous 250 KeV x-ray beams are made to strike the target tissue namely one from 90 degree and another from 270-degrees as another set of simultaneous parallel opposed beams, then all four simultaneous beam's converging total additive LET could be 8 KeV/μ. These simultaneous beams improve the radiation quality and hence it's RBE. If the number of simultaneous beams were increased from four to eight, or sixteen, then the converging additive energy deposited in tissue would increase to 16 KeV/μ and 32 KeV/μ respectively. Hence its RBE also increases. RBE depends on a number of factors, namely radiation quality LET, dose rate, dose, number of fractions, and the biological endpoint.

The additive LET of simultaneous beams improves the radiation quality significantly. The LET of about 100 million-dollar costing a 150 and or higher MeV proton machine is just 0.5.0 KeV/μ, 16 times less than the additive LET as compared above. A radiation therapy machine with such high-energy simultaneous beams combined with radiation sensitizing single session hyperthermia renders a very effective radiation therapy system.

All Field Simultaneous Radiation Therapy and its Interaction with Heat, and Chemotherapy Heat is a radiation sensitizer. Other actions of heat include enhancement of apotosis, induction of mitotic arrest or causing non-apototic cells to dye by necrosis. In fractionated hyperthermia, thermotolerance appears. It is due to synthesis of heat-shock proteins. Single fraction hyperthermia eliminates the thermotolerance. Hence single fraction radiation therapy combined with radiation sensitizing single fraction hyperthermia enhances the cytotoxicity of both radiation and hyperthermia.

Many textbooks and scientific articles describe the synergic effects of hyperthermia, and radiation with or without chemotherapy. It is summarized in chapter 28, Erick J. Hall's textbook of Radiobiology for the Radiologist (4-1, 4-2, 4-3).

They render independent but additive cytotoxicity. Hyperthermia and radiation therapy has different mechanism for cell killing; energy deposited from heat is thousand times greater than the energy deposited by radiation.

Hyperthermia is effective at S-phase of the cell cycle, a cell cycle phase at which the photon radiation is mostly ineffective to cell kill. It is also effective to cells that are nutritionally deficient and hypoxic and to cells with high PH. Radiation is effective at $G_2$ and M phase of the cell cycle. It is less effective to cells that are in $G_1$ and S-phase. After hyperthermia, the cell death is by apoptosis. These qualities of hyperthermia eliminate the need for reoxygenation and the cell being in a cell cycle phase that is sensitive to photon radiation. It facilitates single fraction super high dose rate photon radiation combined with hyperthermia more effective to treat a tumor. In this instance, there is no need for tumor cells being in a radiation sensitive synchrony for combined radiation and hyperthermia to be more effective. It facilitates single fraction super high dose rate radiation therapy more effectively. The sublethal damage repair after hyperthermia can take up to 120 to 160 hours. After the first treatment by hyperthermia, thermotolerance develops. Before the presence of thermotolerance, namely the very first hyperthermia treatment kills more cells than when it is repeated. Hence the first hyperthermia combined with photon radiation has a steeper cell survival curve than their combined subsequent fractionated treatments.

Heat inhibits repair of single strand breaks and chromosome aberrations induced by radiation. It is due to its ability to inhibit the sublethal damage and potentially lethal damage repair. Repair of sublethal damage does not occur if hyperthermia is applied during radiation. The super high dose rate radiation by the method of all field simultaneous radiation also inhibits the lethal and sublethal damage repair. This combined lethal and sublethal damage repair inhibition by super high dose rate radiation and hyperthermia renders photon radiation therapy's cell kill similar to that of high LET radiation. Such combined photon rotation therapy is especially very effective to treat any tumor that is resistant to photon beam radiation, like melanoma, glioblastoma, sarcoma and the like.

Diagnostic Bremsstrahlung X-Ray and Radiation Carcinogenesis

It is known that there is an increased risk of developing cancer from radiation exposure. The very early pioneers in radiation research, Marie Curie and her daughter Irene were thought to have died of leukemia (18). The long term effects of radiation induced cancers includes skin cancer, lung cancer, bone cancer, liver tumors, leukemia, thyroid cancer, breast cancer etc (18). An increased risk of cancer has occurred among longterm survivors of Hiroshima and Nagasaki atomic bombs. On the average, they received 10 to 100 millisieverts (mSv) of radiation exposure (cited in 19) which is equivalent to radiation exposure from 1 CT scan (cited in 19). Patients may receive multiple CT scans over their lifetime (cited in 19). Life time risk from radiation dose from a routine CT scan of the abdomen and pelvis of a young person with polychromatic bremsstrahlung x-ray is very high (19). In a graphic presentation it is shown to be 100% (19). Likewise, it is reported that there is an estimated risk of 1 in 270 women and 1 in 600 men who had CT coronary angiography at age 40 years will develop cancer due to radiation from the CT scan. It is about twice for 20-year-old patients and about 50% lower for 60-year old patients (19). Imaging with monochromatic x-ray renders 100-1000 times superior image quality with much less radiation to the target tissue (2) and thereby minimizing and or elimination high incidence of radiation carcinogenesis from diagnostic radiology.

Advantages of Radiological Imaging with Monochromatic X-Rays

In U.S. Pat. No. 6,687,333, "System and Method for Producing Pulsed Monochromatic X-Rays" by Carroll F. E et al, (2) and in U.S. Pat. No. 7,391,850, Compact, High-Flux, Short Pulse x-ray Source by Kaertner F. X. et al, (3) a number of superior clinical advantages of imaging with monochromatic high-flux short-pulse x-ray beam are described. However, they do not describe a beam storage ring 128 systems from which multiple simultaneous x-ray beams are switched off towards a target that is treated or imaged.

In this invention, each x-ray beam is made to diverge from its focal point towards the target that is imaged. The x-ray beam is attenuated by the tissue through which it passes through. This attenuated beam is well collimated by the arced collimator 110. This attenuated beam is collected by the stationary detectors as shown in FIG. 7 and FIG. 8. Carroll et al describes a method of generating multiple x-ray beams from a single pulse with x-ray beam reflectors such as a deflected beam is copied several times. It is not like the multiple simultaneous x-ray beams with defined focal points as in this invention; in this instance, each of the simultaneous x-ray beams is generated from a segment of the circulating x-ray beam switched off from the beam switching ring 128. Such small sequentially switched stationary x-ray beams with well defined focal point and its attenuated beam after its passage through the tissue is collected in well collimated stationary detectors 114. It improves the image quality significantly. Improving the image quality with multiple well defined and collimated beams for bremsstrahlung x-rays is described in U.S. Pat. No. 7,366,279 by Edi M. P et al (14).

Iodinated Steroids and Iodine k, l, m, n Shell Characteristic Photon and Auger Electron for Imaging and Radiation Therapy The ability to tune the monochromatic high-flux short-pulse x-rays to the binding energy of the K shell is used to detect various elements in the body. Elements that have great affinity binding to tissue thus can be used such K-shell electron radiation for radiation therapy and imaging. A number of steroid molecules could be directly iodinated (15). It includes estrogen, testosterone, cortisone and a number of other steroids (15). Hence, iodinated estrogen and testosterone (15) could be used for tumor specific K-shell characteristic photon and electron radiation therapy and imaging.

Tumor Specific K-Shell Electron Radiation Therapy and Imaging of Estrogen Receptor Positive and Negative Breast and Testosterone Receptor Positive and Negative Prostate Cancer In the U.S. Pat. No. 4,321,208, "Preparation of Directly Iodinated Steroid Hormones and Related Compounds" by this inventor Velayudhan Sahadevan described the directly iodinated estrogen binding to both estrogen receptor of the tumor tissue and to estrogen antiserum (15). There is estrogen receptor positive and negative breast cancer. Likewise, there is androgen receptor positive and negative prostate cancer. Estrogen binds to estrogen receptor in the breast cancer. Testosterone binds to testosterone receptor in prostate cancer.

Both estrogen receptor positive and negative tumors contain estrogen. While developing the estrogen receptor testing on breast tumors in the mid seventeen as a test for elective treatment of patients with breast cancer, this inventor also tested estrogen contents of both estrogen receptor positive and negative tumors (25). The estrogen receptor assay in tumor cytosol was performed by sucrose gradient ultracentrifugation. Tumor cytosol was prepared from the ground tumor specimen. The estrogen content in such cytosol was determined by radioimmunoassay. Both the estrogen positive and negative tumors were found to have measurable amount of estrogen. From this study, it is evident that both estrogen receptor positive and negative tumors bind to estrogen. However estrogen receptor negative tumors may not have the ability to transport estrogen into the cell interior hence its poor metabolic utilization. However, many estrogen receptor negative tumors could transform into estrogen receptor positive tumors (20).

Like the estrogen receptor positive and negative breast cancer, testosterone receptor positive prostate cancer binds to testosterone. Hence testosterone-androgen ablation is one of the major treatment modality for prostate cancer. Like the transformation of the estrogen receptor negative tumor into estrogen receptor positive tumor (20), testosterone receptor negative tumor might transform into androgen receptor positive tumor. Prostate cancer also contains estrogen receptor. Hence treatment of prostate cancer with diethyl stilbesterol (DES), an estrogenic compound or estrogen itself was a common practice in the past.

Directly iodinated estrogen and androgen offers a unique method of iodinated estrogen enhanced, tissue specific, radiation therapy by excitation of iodine bound to estrogen which binds to estrogen receptor positive breast and prostate cancer. Other iodinated steroid molecules like iodinated testosterone bound to testosterone receptor positive prostate cancer offers similar tissue specific receptor bound iodine for iodine's K-shell excitation characteristic photon and Auger resonant electron radiation therapy. Iodinated cortisone (15) is another such example. The iodinated steroid molecule is administrated either intravenously or it is implanted into the tumor as adsorbed on to charcoal nano particle dust. Such implanting of the nano particle charcoal bound iodinated steroid molecule has the advantage of inhibiting the metabolic dissociation of iodine from the steroid and thus preventing dissemination of iodine from the implant site in the tumor.

Like the naturally occurring estrogen, the iodinated estrogen also binds to estrogen receptor competitively with estrogen DES and other estrogen receptor binding anti-estrogen like molecules like tamoxifen citrate. Hence in estrogen receptor positive tumors, the iodinated estrogen will overcome the cell membrane blocks and move into the cell while in estrogen receptor negative tumors, it will be blocked at cell membrane level. Still both estrogen receptor positive and negative tumors will contain iodinated estrogen. In estrogen receptor positive tumors, first it binds to cell membrane. The cell membrane bound iodinated estrogen-estrogen receptor is then transported into the cell. In estrogen receptor negative tumors, it is mostly bound to cell membrane and might not be transported into the cell. Synergistic activation of functional estrogen receptor (ER)-α by DNA methyltransferase and histone deacetylase inhibition in human ER-α-negative breast cancer cells renders a substantial percentage of them as estrogen receptor positive cells (20). Thus the blockage of estrogen transport into estrogen negative tumor cell can be overcome. It facilitates tumor specific K-shell characteristic photon and Auger electron radiation therapy and imaging of estrogen receptor negative tumors as well. The same is applicable to estrogen receptor positive and negative prostate cancer. They are just examples of tumor specific K-shell characteristic photon and Auger electron radiation therapy and imaging. High affinity iodinated cortisone binding tumors are treated similarly with k, l, m, n shell characteristic photon and Auger electron. There are many tumors with high affinity binding to nano particle elements. Such tissue specific high affinity binding to nano particle elements are used for K-shell electron radiation therapy and imaging.

Whole Body Screening for Concealed Objects by Computerized Tomography with Multiple Simultaneous Monochromatic X-Ray and Spent Electron Beams Whole body Computerized Tomography and Radiology with monochromatic high-flux short-pulse x-ray for screening improves the image quality 100 to 1000 times more than imaging with bremsstrahlung radiation. It has many applications including the medical and other applications like screening of a container for its contents and screening of passengers at an airport and the like. A single exposure whole body radiology and CT imaging with multiple simultaneous beams of varying energy can detect items like explosives worn under the cloths with greater efficiency and image quality. The differential pixel analysis of such a class of elements detects the suspect elements and their images. The inverse Compton scattering interaction of electron beams of varying energies with multiple laser beams of varying energies facilitates multiple simultaneous monochromatic beams of varying energies. Exposures of the whole body with such multiple simultaneous beams detect the body parts and the clothing in minor details. Likewise exposure of a container with such multiple simultaneous monochromatic beams detects the contents of a container in minor details. Differential pixel analysis of such exposures with varying energy monochromatic x-rays detects elements of different atomic structure by their differential Auger transformation radiation and their spectrums. In a container analysis, the specific atomic spectrums of Auger transformation radiation of high and low atomic weight substances and its comparison with known Auger emission of high and low atomic weight elements detects suspect elements like uranium or elements used as explosives. It detects the minor details of the fabrics and its composition as well as if it were equipped with instruments for destructive purposes including for explosive purposes. This facilitates split seconds screening of passengers at a busy airport with much higher precision than imaging with a single energy single beam exposure with monochromatic x-ray or with bremsstrahlung x-ray. It is much superior to imaging with varying energy bremsstrahlung x-ray and its spectral pixel analysis (27). Simultaneous monochromatic beams of varying energies and their very high quality imaging facilitate imaging with greater clarity. It also facilitates detection of minor fractures and defects in equipments and instruments made with precision engineering by such high quality imaging and differential pixel analysis of such exposures with tuned monochromatic x-rays of varying energies. Its use thus expands to a wide arena of innovative radiology, both in biomedical applications and in industrial radiology.

BRIEF SUMMARY OF THE INVENTION

Image guided all field simultaneous radiation therapy (AFSRT) overcomes many of the disadvantages of daily subfractionated and overall fractionated radiation therapy. Its high dose rate is achieved by combined isocentric dose rate of all converging beams at the isocenter and not from increasing the machine dose rate to very high that cause major normal tissue toxicity. The imaging is by monochromatic x-ray generated by the inverse Compton scattering interaction of electron and laser photon beams. After the interaction of the electron beam with laser photon beam, the spent electron beam is not wasted as in present the present art of generating monochromatic x-rays. Instead, it is reused for radiation therapy.

The simultaneous monochromatic x-rays are used for both imaging and as external beam radiation therapy. It is also used to generate characteristic auger transformation radiation of heavy elements that are either bound to tissue specific receptors like the directly iodinated estrogen to estrogen receptor or directly iodinated androgenic steroids to steroid receptors in prostate cancer. Alternatively, heavy atom nano particles are implanted into the radiating tissue and they are radiated with tuned monochromatic x-rays to induce its atom specific Auger transformation radiation. The monochromatic beam's energy is tuned to the k, l, m, n shell binding energies of the bound or implanted heavy atom nanoparticles. Such tissue specific radiation elicits the tumor specific radiation therapy. Radiation therapy is also rendered with spent electron beam or with photon that it generates.

Multiple simultaneous electron beams and collilinear monochromatic beams for imaging and radiation therapy are generated by the interactions of electron and laser beams. CT imaging with monochromatic x-ray is performed before, during and after radiation therapy. Imaging with tail end contaminating filtered photon of electron beams or lower energy megavoltage beams are also used for imaging. The image processing with collimated detectors minimizes the scatter radiation induced image distortion.

Screening for concealed objects in the body or in a container is with single or simultaneous multiple beams. In screening mode configuration, treatment modality is removed and the system is used only in imaging mode that is adaptable for screening at places like at airports and at cargo handling places. By imaging with monochromatic x-rays, the image quality is enhanced by a factor of 100 to 1000 times than imaging with bremsstrahlung x-rays. The lower dose whole body radiological screening imaging including with CT scans reduces the total body radiation dose to a passenger or to a patient. It reduces the risk of carcinogenesis than when the imaging is with bremsstrahlung x-rays.

This mode of imaging detects the minor details of the fabrics and its composition as well as if it were equipped with instruments for destructive purposes including for explosive purposes. This facilitates split seconds screening of passengers at a busy airport with much higher precision than imaging with a single energy single beam exposure with monochromatic x-ray or with bremsstrahlung x-ray. It renders much more superior imaging with lesser radiation dose to a person or to an object than imaging with varying energy bremsstrahlung x-rays. Such image's pixel analysis renders superior quality results than the image pixel analysis of bremsstrahlung radiology and CT scans. Simultaneous tuned monochromatic beams of varying energies to image objects of varying atomic number and their very high quality images are used to analyze objects with greater clarity. It detects minor fractures and defects in equipments and instruments made with precision engineering.

The additive high dose rate and additive linear energy transfer from simultaneous beams at the isocenter from multiple angularly placed treatment heads at the isocenter renders photon radiation therapy with much higher radiobiological effectiveness than it is possible by conventional single beam subfractionated and overall fractionated radiation therapy. The intensity modulated radiation therapy is rendered with multiple beams of varying energies. Its beam on time to treat a tumor is only seconds. It also facilitates breathing synchronized radiation therapy without having more complex and expensive equipments to do so. To enhance the effectiveness of the treatment, this all filed simultaneous radiation therapy is combined with hyperthermia and chemotherapy. Such treatment do not need weekly or monthly chemotherapy that in general lasts about six months or more. It itself is great inconvenience to the patient and is indeed very costly.

Multiple simultaneous electron beam segments and its collilinear monochromatic x-rays are switched from octagonal beam lines or from a beam storage ring. The beamlets are deflected at 90 degree towards the isocenter with bending, focusing and switching magnets. The use of magnets that have fast rising time keeps the beam storage ring's diameter short. In the short diameter circular beam storage ring, segments of electron beam and collilinear monochromatic x-ray beam accumulate at each beamlets respective switching points. The beamlets are switched from the beam storage ring with bending, switching and focusing magnets simultaneously into individual beam pipes that leads the beamlets into individual treatment heads and to imaging heads.

The isocentric additive high dose rate from simultaneously converging multiple beams, the concomitant hyperthermia and chemotherapy and tumor specific radiation therapy and the AFSRT's very low radiation to the normal tissue all are used to treat a tumor with lower radiation dose and also to treat a radioresistant and or multiple times recurrent tumors that heave no other alternative treatments.

BRIEF DESCRIPTION OF THE DRAWINGS

FIG. 1A: Illustrates an electron beam producing accelerator, electron beam interacting with laser photon beam that produce the inverse Compton scattering high-flux short pulse x-ray and the deflected monochromatic x-ray and the dumped electron beam.

FIG. 1C: Is a further modified illustration of the separated electron beamlets without electron beam and infrared laser beam interaction to produce monochromatic high flux-short-pulse x-rays.

FIG. 10A: shows the beam storage ring 128 from which synchronized multiple simultaneous electron and monochromatic x-ray beams are switched off for all filed simultaneous radiation therapy and imaging.

FIG. 10D: Illustrates collilinear electron beam and the monochromatic x-ray beam traveling together in the forward direction of the electron beam and as they are not separated for injection into a beam storage ring.

REFERENCE NUMERALS

Figure 1B:
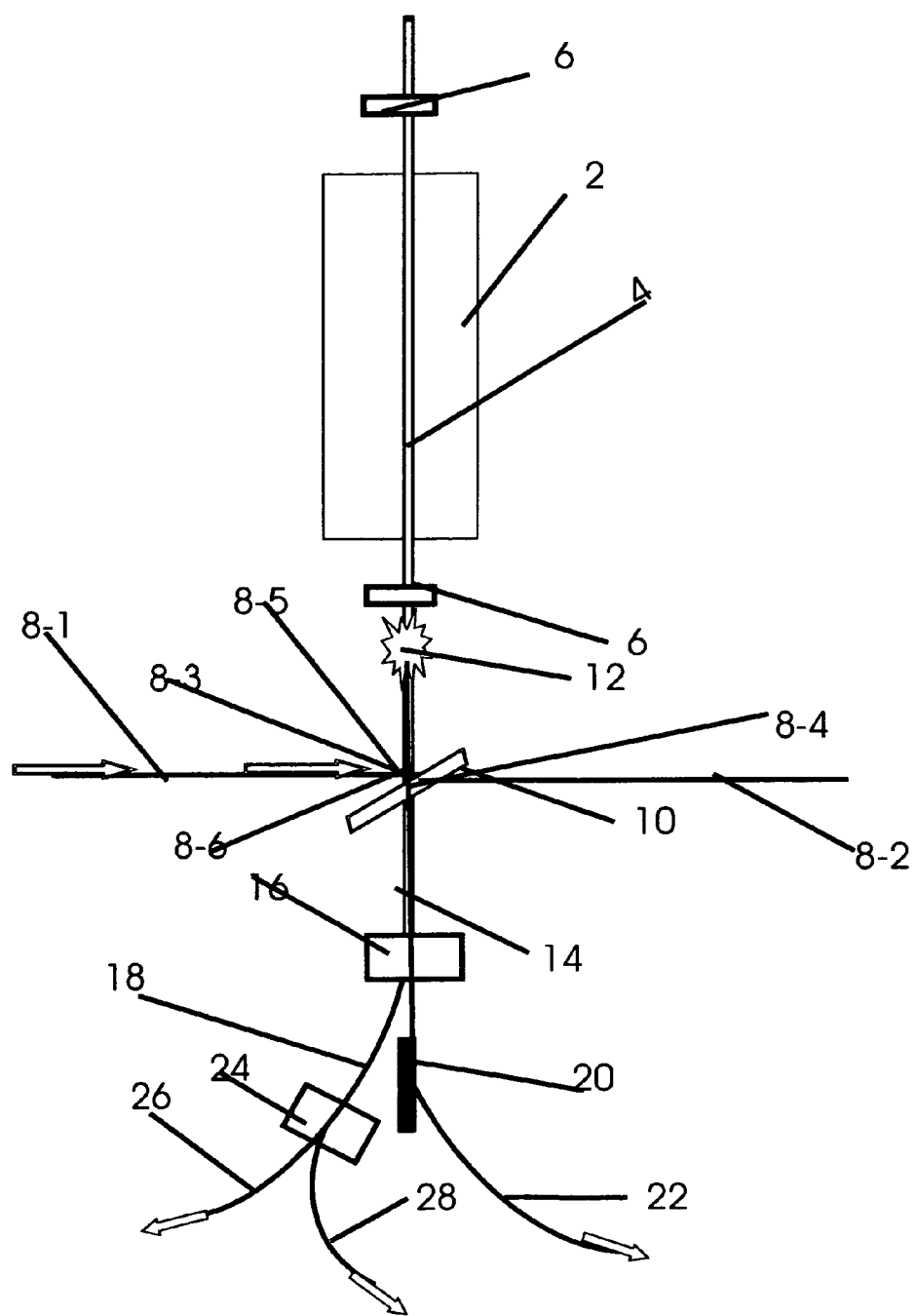
FIG. 1B: Shows the inverse Compton reaction of electron and laser photon beams as in FIG. 1A but the electron beam is switched into two beamlets, one to the right and the second to left.

2. Accelerator
4. Electron beam
6. Focusing magnet
8-1. laser beam-1
8-2. laser beam-2
8-3. laser beam-3
8-4. laser beam-4
8-5. laser beam-5
8-6. laser beam-6
10. Beryllium mirror
12 Electron beam and infrared laser beam interaction
14. Inverse Compton scattering's collilinear x-ray and electron beams
15. Quadrupole focusing magnet
16 Electron beam deflecting magnet
18. Deflected spent electron beam
20. Graphite mosaic crystals
22. Deflected monochromatic x-ray beam
24. Beam switching magnet-1
26. Split spent electron beam-1
28. Split spent electron beam-2
32. To right focusing magnet
34. To left focusing magnet
36. To right 45 degree bending magnet
38. To left 45 degree bending magnet
40. 11.25 degree bending magnet-1
42. Quadrupole focusing element-1
44. 11.25 degree bending magnet-2
46. Switching magnet S-2
48. 45 degree bending magnet-1
49. Beam outlet
50. Quadrupole focusing element-2
52. 45 degree bending magnet-2
54. Beam transport pipe
56. 22.5 degree bending magnet-1
58. Quadrupole focusing element-3
60. 22.5 degree bending magnet-2
62. Stationary phase contrast imaging unit
64. Monochromatic x-ray collimator
66. Octagonal beamline
67. Bending and focusing magnets
68. Switching magnet 3
70. Stationary treatmenthead-1
72. Switching magnet 4
74. Stationary treatmenthead-2
76. Switching magnet 5
78. Stationary treatmenthead-3
80. Switching magnet 6
82. Stationary treatmenthead-4
84. Switching magnet 7
86. Stationary treatmenthead-5
88. Switching magnet 8
90. Stationary treatmenthead-6
92. Switching magnet 9
93. Electron beam switching magnet 94. Stationary treatmenthead-7
96. Table
98. Beamline 1
100. Beamline 2
102. Switching magnets 10-25
104. Stationary treatmentheads 8-23
106. Isocenter
108 Stationary tilted treatment heads 24-39
110. Arced collimator
112. Collimated beam guide
114. Stationary detectors
116. Exiting divergent beam
118. Collimated exiting divergent beam
120. Collimating beam guide
122. Stationary detectors holding ring
124. Signal processing system
126. Stationary electron cone 1-16
128. Beam storage ring
130. Beam input magnet
132. Bending magnet
133. Collilinear spent electron beam and monochromatic x-ray beam
134. Bent and focused electron and x-ray beam
134. Injection beam line
135. Fast magnetic switch
136. Beam switching point
138. Therapy unit's treatment head
140. Imaging x-ray unit's head
142. Spent electron beam
145. Electron and monochromatic x-ray beam segments
146. Graphite mosaic crystals
148. Deflected x-ray beam
150. Rotateable x-ray deflecting mirror
152. X-ray beam absorber
154. Rotating Gantry
156. Electron gun
158. Linear accelerator
160. Focusing element quadruple element
162 achromatic magnet
164. Collimator
166. Ion Chamber
168. Laser source-1
170. Laser source-2
172. Mirror
174. Electron dump
176. Motor shaft
178. Motor
180. Object
182. Table
184. Detector array
186. Detector elements
188. Post reaction electron beam
190. Graphite mosaic crystals
192. Deflected monochromatic x-ray beam
194. X-Ray absorber

DESCRIPTION OF THE PREFERRED EMBODIMENTS

FIG 1A: Illustrates an electron beam producing accelerator, electron beam interacting with laser photon beam that produce the inverse Compton scattering high-flux short pulse x-ray and the deflected monochromatic x-ray and the dumped electron beam. It is a partial schematic representation of the general principles on producing inverse Compton scattering high-flux short pulse x-ray that is described in U.S. Pat. No. 7,391,850 and U.S. Pat. No. 6,687,333. They are referred herein in their entirety. FIG. 1A: illustrates the general principles involved in building a compact source for monochromatic high flux-short-pulse x-rays. Briefly, electron beams produced in a photocathode is focused with the focusing magnet 6 and injected into the accelerator 2. As the electron beam exits the accelerator 2, it is focused again with a second focusing magnet 6 before the electron beam interacts with an infrared laser beam 8 which is deflected with the mirror 10 towards the opposing direction of the electron beam 4. More than one laser beams, 8-1, 8-2, 8-3, 8-4, 8-5, 8-6, of varying wave lengths are used to obtain tuned, varying energy monochromatic x-rays. Alternatively, the electron beam energy is varied to tune the monochromatic x-ray's energy. The electron beam 4 and the infrared laser beam 8 collide with each other. By this electron beam and infrared laser beam interaction 12, the infrared laser photon is converted to monochromatic high flux-short-pulse x-rays. This x-ray beam travels almost collilinear with the electron beam's forward propagation. The inverse Compton scattering's collilinear x-ray and electron beams 14 travels together. The electron beam is separated from the monochromatic high flux-short-pulse x-rays with the electron beam deflecting magnet 16. The monochromatic high flux-short-pulse x-rays is deflected with graphite mosaic crystals 20 at shallow angles. It renders deflected monochromatic high flux-short-pulse x-ray beam 22. The deflected spent electron beam 18 is dumped away and is absorbed by the electron beam absorber 19. It is treated as a waste product in of the inverse Compton scattering monochromatic high flux-short-pulse x-ray generation process. In this invention, this otherwise wasted deflected spent electron beam 18 is reused as a source for all filed simultaneous radiation therapy combined with imaging with monochromatic high flux-short-pulse x-rays.

Figure 6:
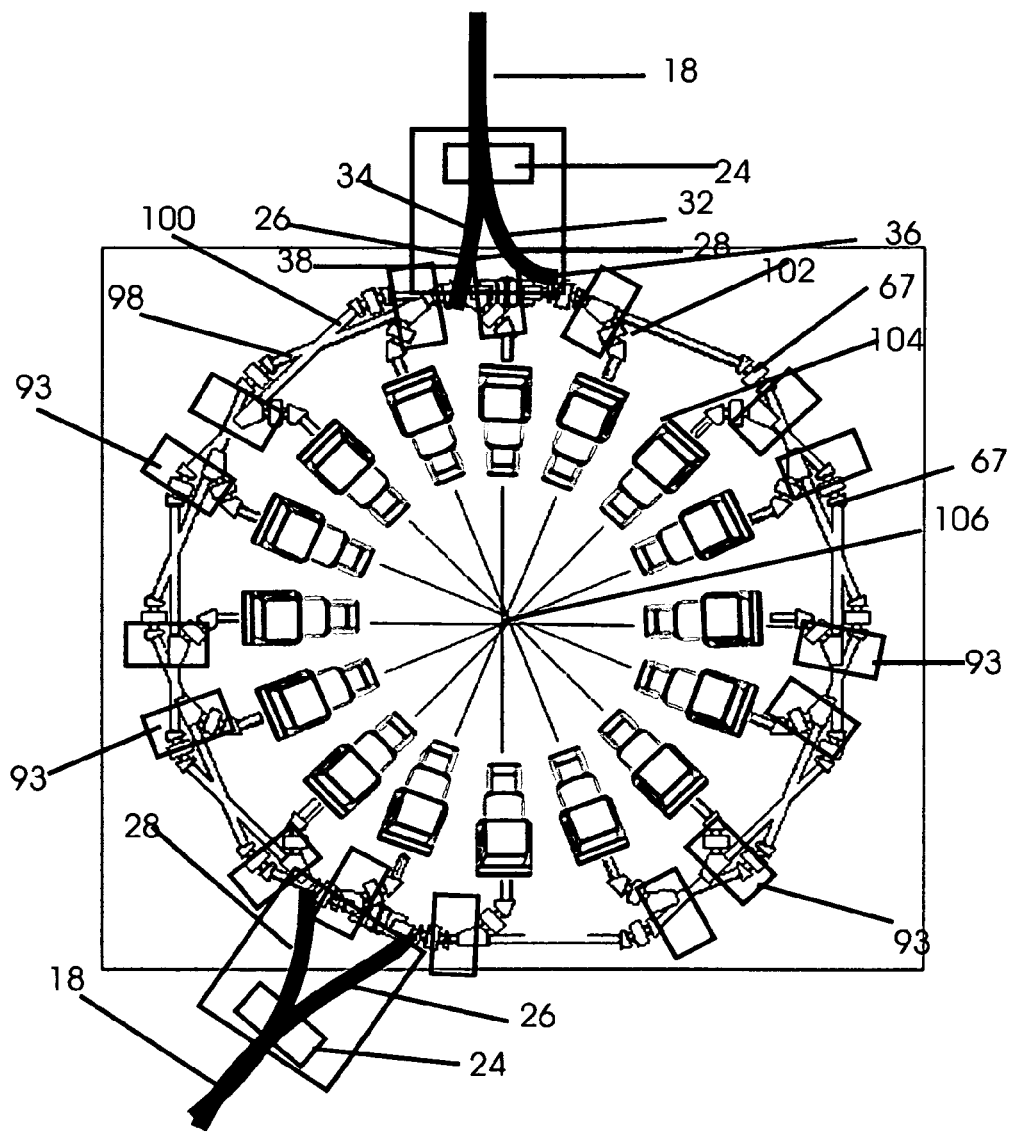
FIG. 6: is an illustration of the switched electron beams to right and left and they are steered into two octagonal beam lines with sixteen beam outlets to which sixteen treatment heads are attached.
Figure 7:
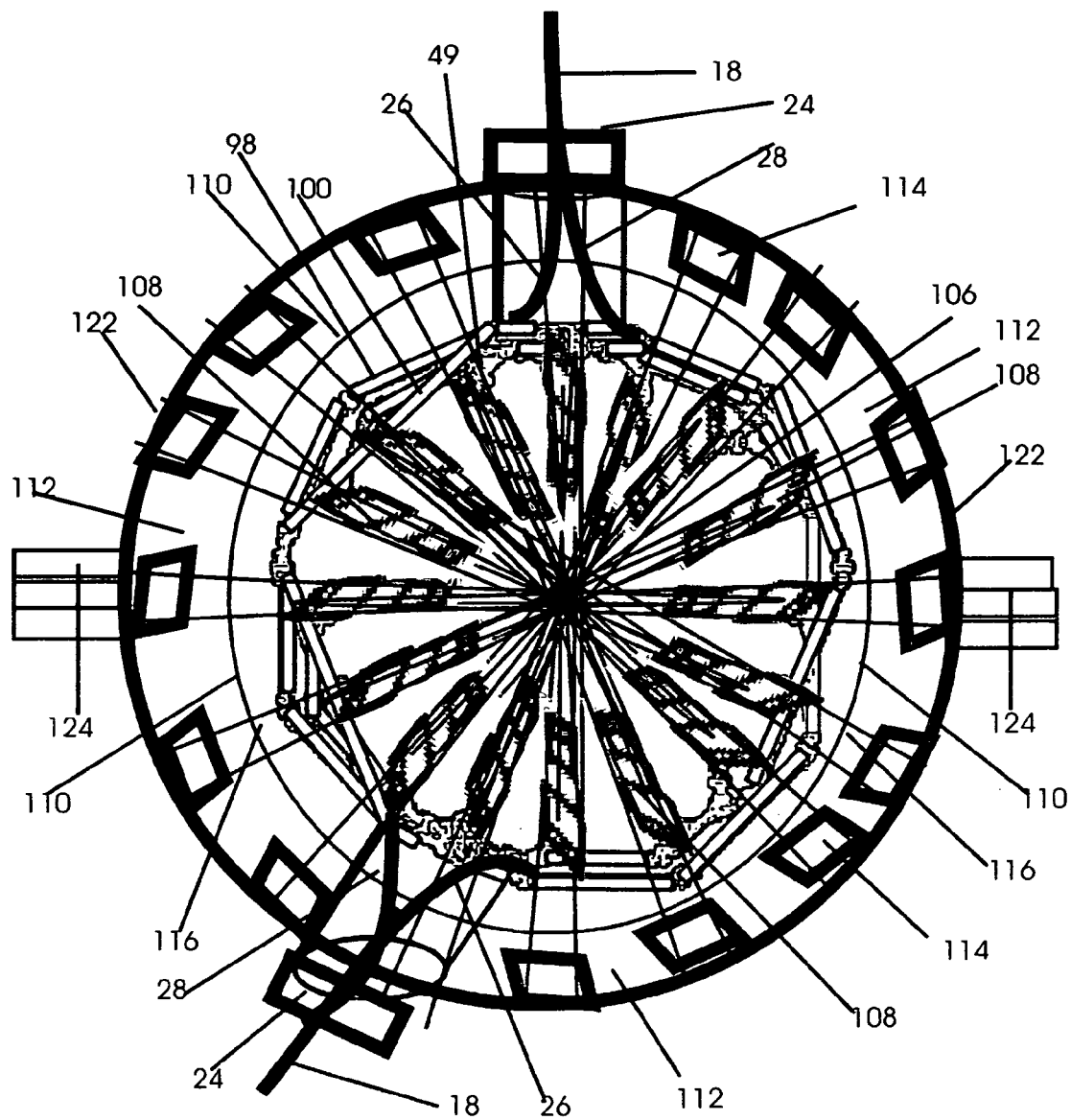
FIG. 7: Illustrates the same sixteen beamlets and sixteen treatment heads as in FIG. 6 but the treatment heads are tilted plus or minus five degrees to allow the exit beam to strike the parallel opposing detectors attached to the detectors holding ring that is placed outside the beamlines with the treatmentheads.

FIG. 1B: Shows the inverse Compton reaction of electron and laser photon beams as in FIG. 1A but the beam absorber is removed and in its place a beam switching magnet is placed that switches the electron beam to the right and to left. The beam switching magnet-1, 24 separates the electron beam into two separate beamlets, split spent electron beam-1, 26 and the split-spent electron beam-2, 28. Such separated double beamlets are injected into double octagonal beam lines as illustrated in FIG. 6 and FIG. 7. They serve as one of the electron source for all field simultaneous radiation therapy. Otherwise, all the other structures are the same as in FIG. 1A and FIG. 1B.

FIG. 1C: Is a further modified illustration of the separated electron beamlets shown in FIG. 1B but without electron beam and infrared laser beam interaction to produce monochromatic high flux-short-pulse x-rays. The electron beam is switched into a right and left beams by the electron beam deflecting magnet 16 for all filed simultaneous radiation therapy as in FIG. 6 and FIG. 7. In this instance, no inverse Compton Scattering monochromatic high flux-short-pulse x-rays is generated by the interaction of the electron beam and the infrared laser beam. Otherwise, all the other structures are the same as in FIG. 1A and FIG. 1B.

Figure 1D:
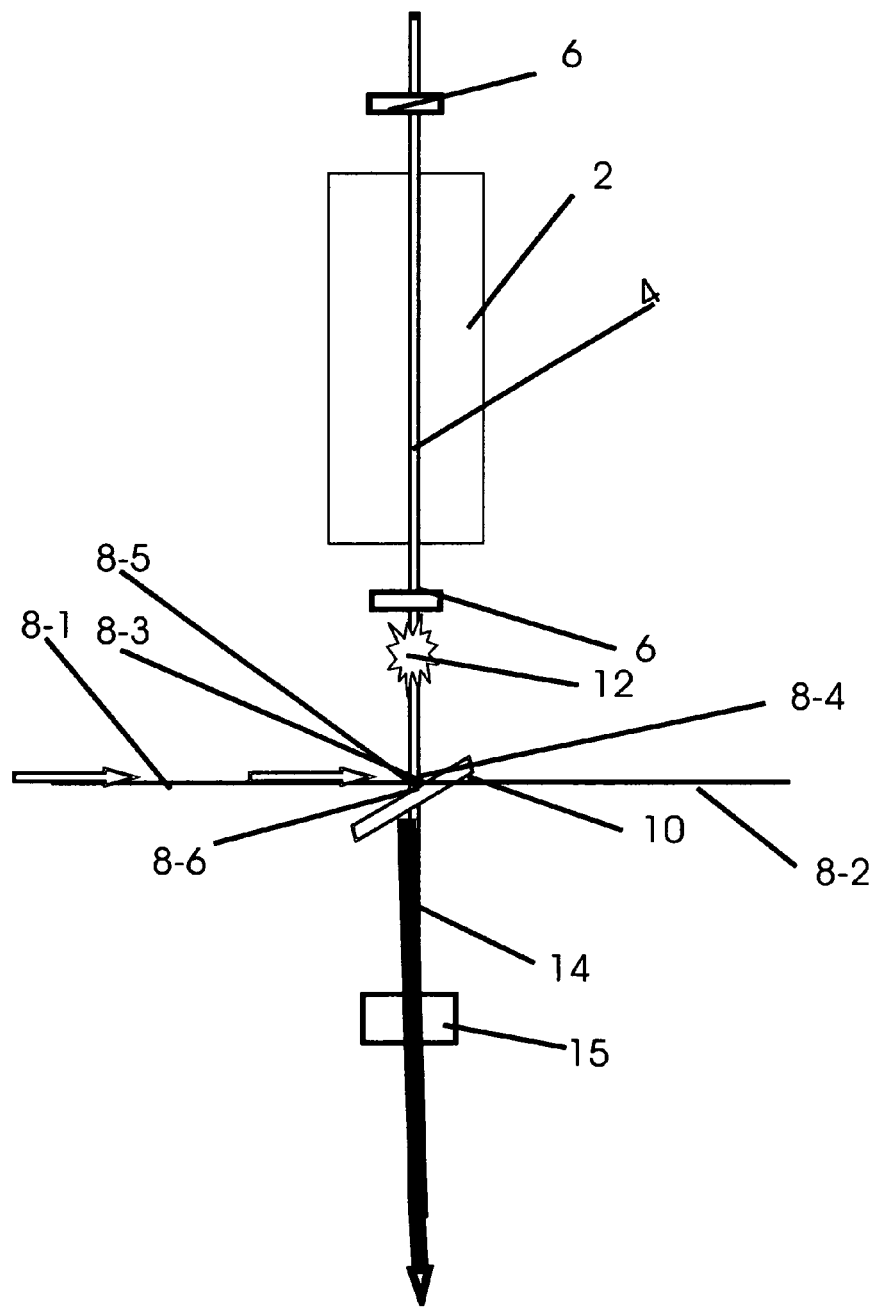
FIG. 1D: Illustrates collilinear electron beam and the monochromatic x-ray beam traveling together in the forward direction of the electron beam and as they are not separated for injection into a beam storage ring FIG. 2 Is another illustration of switching the electron beam into right and left beams and steering them into the beam lines with steering magnets FIG. 3 Illustrates a section of the beam line with steering magnets that bends the beam 90 degrees to the right or left FIG. 4 Shows the components used to bend the electron beam to 22.5 degree to steer the beam towards the treatment head at 22.5 degree

FIG. 1D: Illustrates collilinear electron beam and the monochromatic x-ray beam traveling together in the forward direction of the electron beam and as they are not separated for injection into a beam storage ring. The inverse Compton scattering's collilinear spent electron and x-ray 14 shown as a single beam. It is focused with quadrupole focusing magnet 15 before its injection into the beam storage ring 128.

FIG. 2 illustrates the deflected electron beam after the inverse Compton interaction of the electron and the laser photon beam. The beam switching magnet 24 switches the beam to left 26 and to right 28. The focusing magnets 32 and 34 focus these switched electron beams. Bending magnets 36 and 38 steers the beam to the right and left with a 45-degree bending.

Figure 3:
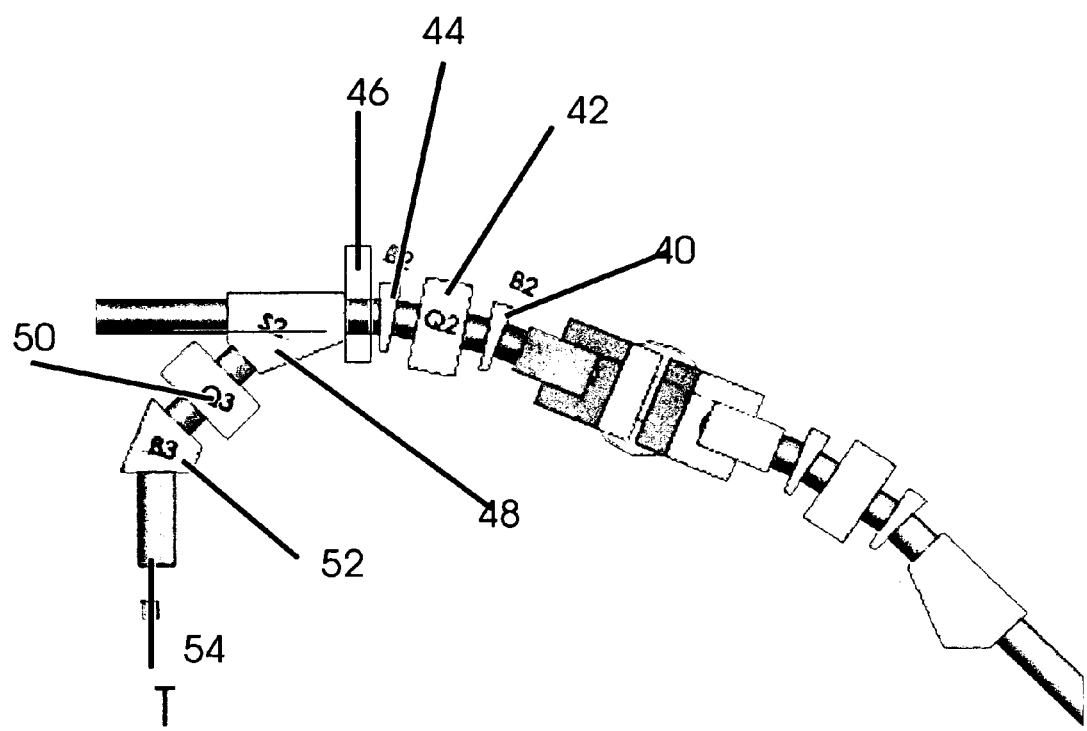

FIG. 3: illustrates the 90° bending of the electron beam traveling through the beam line towards the target, 54. The 11.25° bending magnet-1, 40, the quadrupole focusing element 42, another 11.25° bending magnet-2, 44, and the beam switching bipolar magnet 46 to steer the beam through the beam line is shown. The bending and focusing magnets 40, 42 and 44 bends the beam to 22.5°. The beam switching bipolar magnet 46 switches the beam at 15-degree angle divergence. One of the switched beams is made to make a 45° bend when the bending magnet 48 is activated. It is then made to travel towards the target by the beam steering system magnets consisting of 48, 50, and 52 where the steering magnet 48 is a 45 degree bending magnet-1, 50 is a quadruple focusing element, and 52 is a 45 degree bending magnet-2. The beam is thus bent to 90° and made it to strike the target 54 to generate the photon beam. If it were an electron beam treatment, the target 54 is moved away from the path of electron beam. The other segment of the split beam is steered towards the next treatmenthead station through the octagonal beamline.

Figure 4:
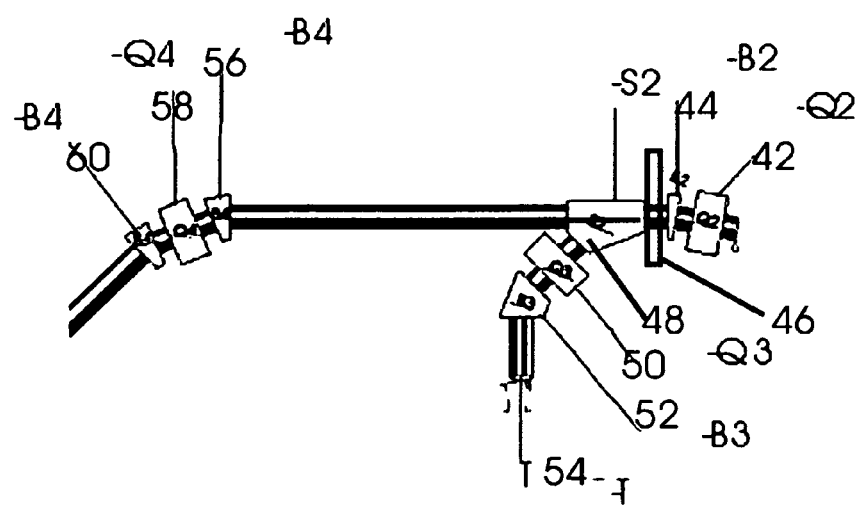

FIG. 4: Illustrates the components for steering the beam towards the next treatment head. It shows the two 22.5 degree bending of the beam to make a combined 45 degree bend to guide the beam through the octagonal beam line. One of the switched beams by the switching magnet 46 is steered towards the target 54 in the treatment head by the steering magnets 48, 50, and 52. The other switched beam is steered through the octagonal beam line to its next 45 degree bending site. It is accomplished with a 22.5 degree bending magnet-1, 56 and it's focusing with a focusing quadrupole element 58 and another 22.5-degree bent with the bending magnet-2, 60. When this beam reaches the next treatment head, location, it is again switched as two beams as before by the switching magnet. One segment of such beam is steered towards the next treatmenthead and another segment of the switched beam is steered towards the next treatment station.

If treatment by a treatment head is to be bypassed, the beam switching bipolar magnet 46 of that station and that station's beam steering towards the target 54 in the treatmenthead in that location by the beam steering magnets 48, 50, and 52 are switched off. In this instance, the beam is steered to the next treatment head station through the octagonal beam line as described before. Such beam switching at each treatmenthead station and steering of one of the switched beam towards the target in a treatment head and steering of the another switched beam through the octagonal beam line towards the next treatmenthead station allows all field simultaneous radiation therapy of a tumor in a patient. If the radiation is by electron beam only, then the target 54 is moved away from the path of electron beam. In combined simultaneous electron and photon beam treatment mode, the target is moved away from the electron beam's path in those treatmentheads where a field is treated by electron beam and the target is inserted where a field is treated by photon beam.

Figure 5:
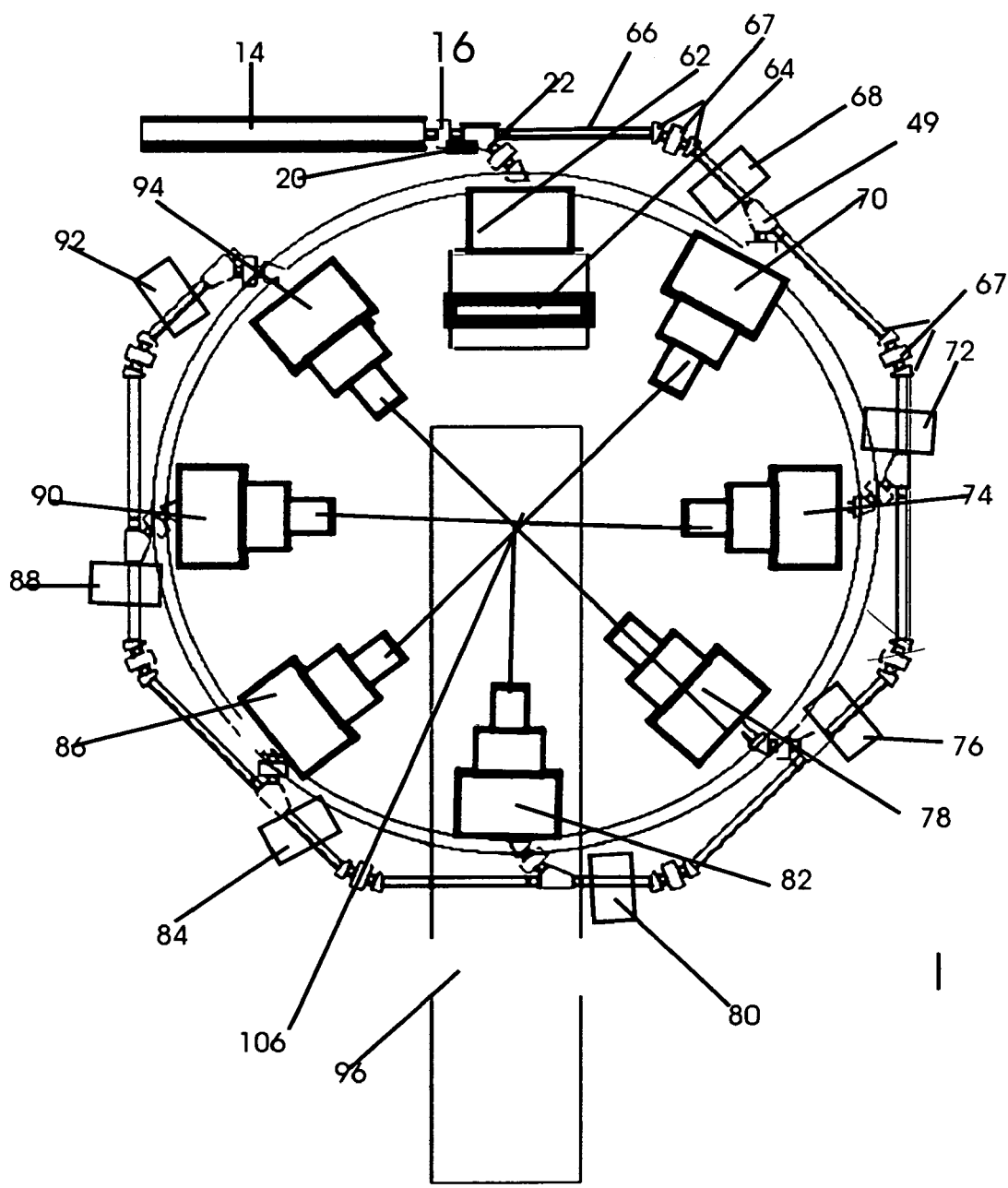
FIG. 5: Illustrates the inverse Compton reaction's electron beam steered through an octagonal beamline to seven treatmentheads and the phase contrast x-ray unit

FIG. 5: shows the inverse Compton reaction's electron beam 14 steered through an octagonal beamline 66 to seven stationary treatmentheads and the stationary phase contrast x-ray unit 62. Six of the stationary treatment heads are arranged as pairs of parallel opposing ones. One stationary treatment head is arranged as parallel opposing to the phase contrast imaging unit 62. As described before, the beam switching bipolar magnets 68, 72, 76, 80, 84, 88 and 92 are used to switch the electron beam into two at each treatment head stations. One of the switched electron beam is steered to the treatmenthead by steering magnets 48, 50 and 52. The other switched electron beam is steered through the octagonal beam line by the bending and focusing magnets 67 which includes the bending magnets 56 and 60 and the focusing magnet 60. The bending and focusing magnets 67 steers the electron beam through the beam line at each bends of the octagonal beam line 66. The stationary treatment heads 70, 74, 78, 82, 86, 90 and 94 are attached to the octagonal beam line 66. The beams from the treatment heads are focused at the isocenter 106 that is shown as falling on to the imaging and treatment table 96.

FIG. 6: is an illustration of the switched electron beams to right and left and they are steered into two octagonal beam lines with 16 beam outlets to which 16 treatment heads are attached. The electron beam 18 is either the electron beam from the inverse Compton reaction with laser photon or a separate electron beam produced in the accelerator 2. The two octagonal beam line one 98 and the octagonal beamline two 100 have combined 16 beam outlets. The electron beam 18 at 0-degree and the electron beam 18 at 202.5° are switched to right and left by the switching magnets 24. As described before, at each treatment stations a beam switching magnet 93 switches the electron beam to right or left. One of the switched electron beams is steered towards the target 54 in a stationary treatmenthead 104 by 45 degree bending magnets-1 48, quadrupole focusing magnet-2 50 and the 45 degree bending magnet-2 52. The other switched electron beam is steered through the octagonal beam line by the bending and focusing magnets 67 which includes the 22.5 degree bending magnets 56, quadrupole focusing element-3, 58 and 22.5 degree bending magnet-2, 60. The bending and focusing magnets 67 steers the electron beam through the beam line at each bends of the octagonal beam lines 98 and 100. Sixteen parallel opposing stationary treatment heads 104 are attached to both octagonal beam lines 98 and 100. The beams emerging from the stationary treatment heads 104 are focused at the isocenter 106.

If it were sixteen fields, single session, 800-cGy-radiation therapy or radiosurgery, with sixteen beams, the dose delivered at the isocenter 106 by each beam is 50 cGy. A beam with the dose rate of 400 cGy/min and with the following treatment parameters, average tissue maximum ratio (TMR) 0.746, collimator scatter factor $(S_c)$ 0.98, phantom scatter factor $(S_p)$ 0.99, and the isocenter distance from the source 100 cm has 289.5 cGy at the isocenter. It is described before. The time to deliver 50 cGy by each beam is then 50/289.5 min or 0.1727 min or 10.363 seconds. An alternative calculation could be made as the following. With the $D_{iso}$ dose rate of 289.5 cGy/min, the sixteen beam's additive biological dose rate at the isocenter is 4,632 cGy/min. The isocentric tumor dose is 800 cGy. Hence the time to deliver 800 cGy to the isocenter by each beam is 800/4,632 min or 0.1727 min or 10.363 seconds. A patient with no acute respiratory symptoms can hold breathing during this 10.363 seconds radiation easily. It enables breathing synchronized precision radiation therapy much easier. From the above, it can be derived that if the accelerator dose rate is decreased from 400 cGy to 200 cGy, 100 cGy or 50 cGy, then the additive biological dose rate at the isocenter is 2,316, 1,158, 579 cGy. Hence the beam on time to treat all the sixteen fields simultaneously is 800/2,316, 800/1,158 and 800/579 min respectively. It is then 20 seconds, 41.45 seconds and 82.9 seconds respectively.

FIG. 7: Illustrates the same sixteen beamlets and sixteen stationary treatment heads 104 as in FIG. 6 but the treatment heads are tilted plus or minus five degrees to allow the stationary exiting divergent beam 116 to strike the stationary detectors 114 attached to the stationary detectors holding ring 122 that is placed outside the beamlines with the treatmentheads. Each of the exiting stationary divergent beams 116 functions as an x-ray source for imaging. As in FIG. 6, two octagonal beam lines, 98 and 100 with 16 beam outlets 49 to which 16 stationary treatment heads 108 are attached, but the treatment heads are tilted to about plus or minus five digress avoid the exiting divergent beam's blockage by the beam lines and the opposing treatment heads. Each pairs of the tilted stationary treatmentheads 108 are arranged as parallel opposing ones.

The stationary exiting divergent beams 116 are shown as exposing the stationary detectors 114 attached to the stationary detector holding ring 122. The stationary exiting divergent beams 116 are collimated by the arced collimator 110 and collimating beam guide 120. The arced collimator 110 made of high atomic number elements like lead or tungsten. The collimating beam guide 120 is also made of high atomic weight elements and they are coated with x-ray absorbing membrane like silicon to minimize the scatter radiation reaching the stationary detectors 114 from the stationary tilted treatment heads 108. Time sequential sampling for the multiple simultaneous beams reaching the stationary detector 114 further improves the image quality. The detectors are selected from the group of scintillation based detectors, photon counting detectors or energy discriminating detectors. The scintillation based detector's photodiodes converts the x-ray photon to lower energy charge and to a pixel. It measures the radiation attenuation at each pixel locations. Such data is further processed by the signal processing system 124 and the image reconstruction system (not shown).

With such multiple collimated simultaneous beams, minimal scatter radiation reaching the detectors and with time sequential sampling of x-ray signals in the detectors improves the image quality several folds than the present image guided radiation therapy with single beam megavoltage or kilovoltage CT (MVCT or kVCT). The scatter radiation reaching the detectors distorts the image and the image quality. In addition, the image quality is further improved with monochromatic x-rays reaching stationary detector 114.

Figure 8:
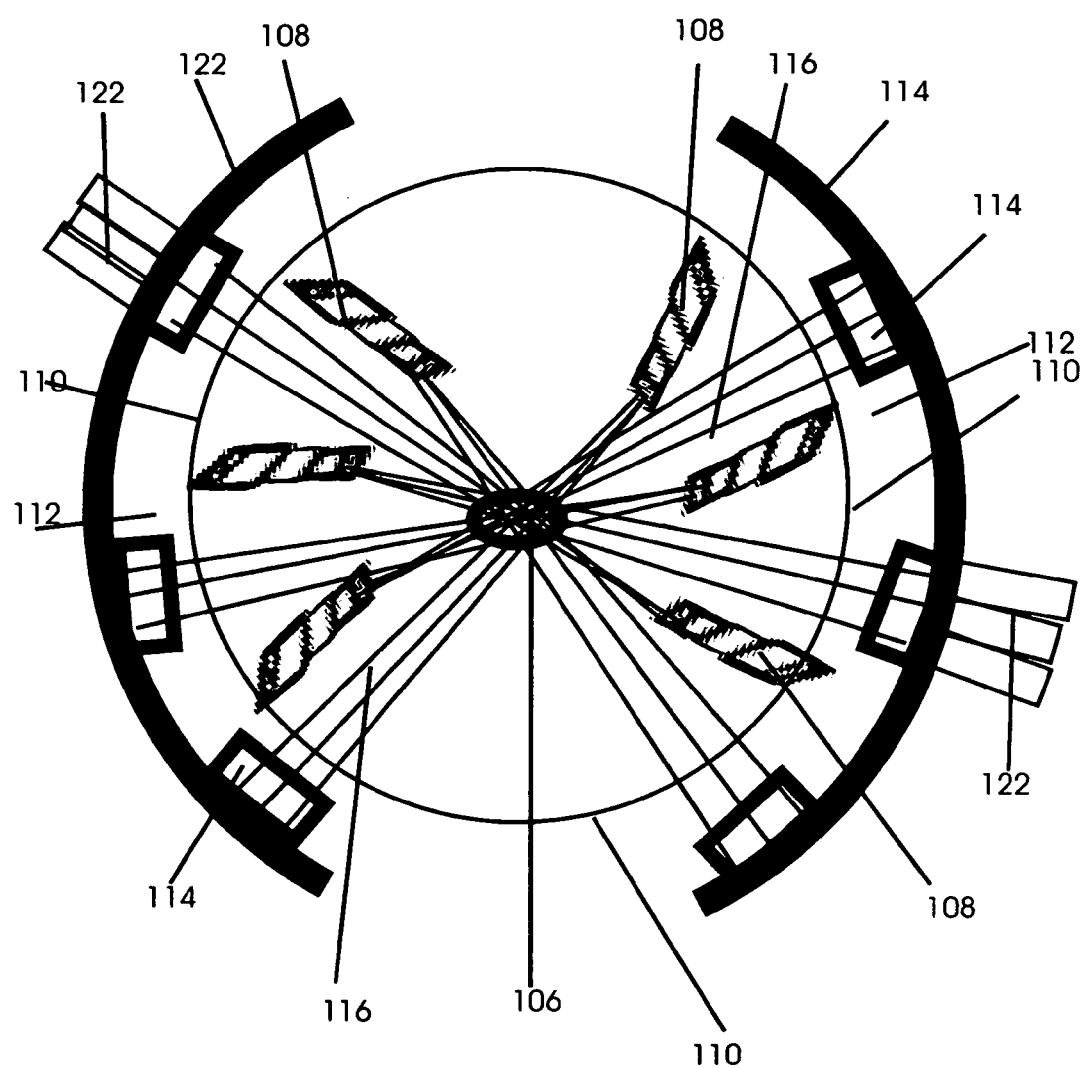
FIG. 8: shows a section of FIG. 7 with multiple collimated stationary detectors and their exposure to multiple simultaneous attenuated exiting divergent beams from stationary tilted treatment heads.

FIG. 8: shows a section of FIG. 7 with multiple collimated stationary detectors 114 and their exposure to multiple simultaneous attenuated exiting divergent beams (116) from stationary tilted treatment heads 108. The stationary exiting divergent beams 116 are collimated with arced collimator 110 and the collimating beam guide 120. Multiple simultaneous beams from multiple stationary tilted treatmentheads 108 are shown as passing through the isocenter 106. It renders high biological dose rate at the isocenter.

Figure 9:
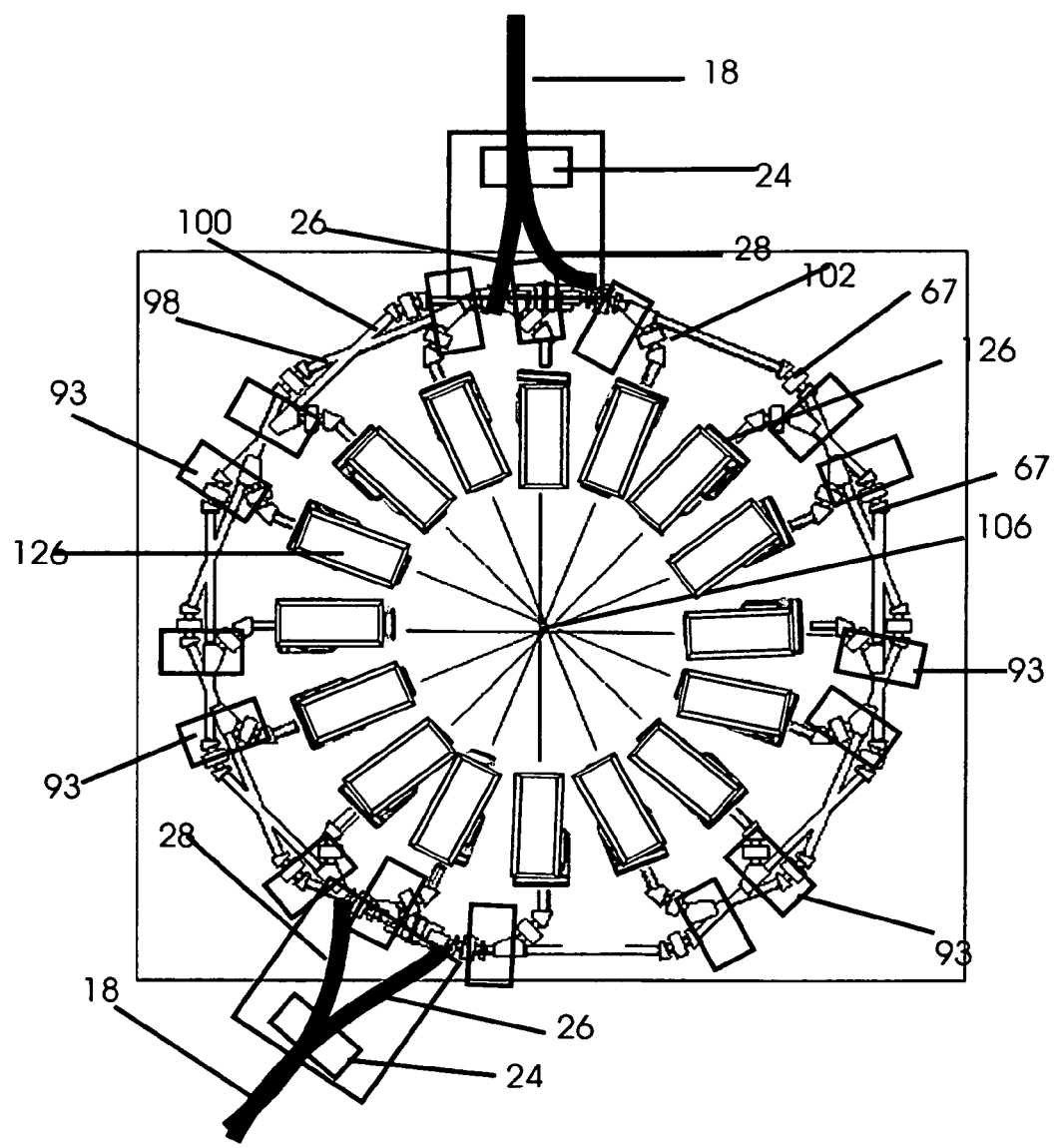
FIG. 9: illustrates the stationary treatment heads shown in FIG. 6 as further modified with an electron cone for high energy electron beam radiation therapy.

FIG. 9: illustrates the stationary treatment heads shown in FIG. 6 but with attached electron cones 126 for photon or high energy electron beam radiation therapy. The beam is flattened either by magnetically scanning or with dual foil system (6) (not shown). The potential electron beam's overlap associated high dose region is managed by adjusting the treatment plan to a uniform combined dose distribution (7). In the electron mode treatment, the changes in dose rate introduced by the effect of field shaping blocks is likewise compensated either with special dosimetry by measuring the output factor, depth dose and isodose distribution for mostly used irregularly shaped fields and storing them for computer assisted dosimetry in general or simply by using the ICRU suggested method of using the practical range $R_p$ as the limiting lower field diameter above which the electron beam's field size dependent changes in depth dose rate is negligible. (8). The multiple stationary tilted treatment heads 108 with attached electron cones are arranged at 22.5 degree angles in the case of a sixteen stationary treatment heads system, or at 45 degree angles in the case of an eight stationary treatment heads system. It allows electron beam pseudoarc method of radiation therapy. In this technique of electron pseudoarc treatment, the field is defined by the jaws in the treatment head. The electron collimation is made on the skin surface of the patient. From equally spaced angels, the beam is directed towards the isocenter. At the center of a given filed, the beam overlaps with the edge of its next neighboring field. This pseudoarc technique renders the treatment results like that of a continuous electron arch treatment (9). The electron arc treatment method is known to provide excellent dose distribution for treating superficial tumors (9).

All the other structures illustrated in this FIG. 9 are identical as in FIG. 6. This multiple simultaneous high energy electron or photon beams configuration facilitates radiation therapy with photon or high energy electron greater efficiency. In high energy electron mode only treatment, it provides sufficient $D^{max}$ dose at the isocentric depth, the dose within the 90 and 80 percent isodose. It eliminates the exit dose contribution at the opposite side except for the contaminating x-rays at the electron beam's tail end. The x-ray contamination is caused by bremsstrahlung interactions of electrons on its way from the accelerator window, through the scattering foil, chambers, collimating systems, the air and with the tissue in a patient that is radiated etc. Such x-ray contamination dose of 30 to 50 MeV electron beam is in the range of 2.8 to 6 percent of the $D^{max}$ dose (5). This contaminating forward moving bremsstrahlung x-ray beam reaches the opposing stationary detectors shown in FIG. 7 and FIG. 8. The electron beam's range at this point is zero. Its backward deflecting K x-ray could be harnessed for mono-energetic x-ray imaging including for phase contrast imaging. However, due to high energy electron beam used for therapy, its contamination with bremsstrahlung x-ray is high but this can be overcome by using only the backward scattering K x-ray and collecting data only from it. By the configuration with the stationary tilted treatmentheads 108 as shown in FIG. 7 and FIG. 8 and attaching the electron cone to such stationary tilted treatmentheads 108, the electron beam's tail end contaminating bremsstrahlung photon beam is made to strike the stationary detectors 114. This beam is collimated to minimize the scattered x-ray reaching the stationary detectors 114 as illustrated in FIG. 7 and FIG. 8.

The advantages of radiation therapy only with high energy electron beam include the followings. It eliminates the needs for heavy shielding as is needed for a photon beam accelerator. It is a significant advantage for a radiation therapy system with stationary treatment heads ranging from 4 to 32 for all field simultaneous radiation therapy. An electron beam treatment facility needs only very simple shielding requirements as compared to shielding requirements for a photon beam treatment facility. Using the rule of thumb, the minimum lead thickness required to block the electron beam in millimeters is electron beam divided by 2 (10). Thus 30-50 MeV electron beam's shielding is accomplished with 1.5 to 2.5 cm thick lead. Hence 3 to 5 cm thick lead shielding is twice more than adequate shielding for 30 to 50 MeV electron beams. Hence, adequate shielding can be achieved even with lead glass. Such low shielding requirement also facilitates building shared mobile all filed simultaneous electron beam radiation therapy system combined with online imaging. Such capabilities are not available with much more expensive other form of machines including with proton radiation therapy machines. In communities with several healthcare facilities with active oncology programs, such shared mobile radiation therapy systems brings the investment requirement for advanced radiation therapy capability much lower while meeting all such institutions needs to render radiation therapy and cancer treatment with cutting edge technology.

As described before, the external beam radiation therapy with electron beam only would eliminate the about 45% exit dose contribution to the opposite side of the skin and surrounding tissue as in the case of radiation therapy with parallel opposing photon beam. Furthermore, the electron beam does not generate contaminating direct neutron beam or by its interaction with a patient as the photon beam does. The 90 and 80% isodose level of the electron beam is approximately E/3.2 and E/2.8 (11). Hence the 30 MeV electron beam's useful treatment depth at 90 and 80% isodose level is about 10 and 12.5 cm. It is a sufficient depth dose for treating most patients. Taking the loss of electron energy at a rate of about 2 MeV/cm of water or soft tissue, the 30 MeV electron beam's range is about 15 cm (11). Hence the 30 MeV electron beam's dose contribution to the opposite side of an average person with 20 cm circumference is negligent except for its small amount of x-ray contamination (5). As the electron beam's energy is further increased from 30 MeV, its 90-80% isodose level and the range of its contaminating x-ray at its isodose curve's tail end will also increase. This gives sufficient depth dose to treat a larger sized patient. In this instance, the range of the contaminating x-ray beam of the electron beam reaching the opposite side of the patient will also increase. It will thus reach the image processing stationary detectors 114 attached to portions of the stationary detector holding ring 122 that is closer to the opposite side of the patient. The electron beam passes through the patents; it is absorbed and filtered which renders mostly filtered forward transmitting bremsstrahlung x-ray for imaging.

Alternatively, this configuration of all field simultaneous radiation therapy system could be combined with imaging with monoenergetic K-x-ray. In this instance, lower energy electron beam in the range of 1 to 4 MeV is used to generate backward transmitting monoenergetic K x-ray. Such monoenergetic K-x-ray could also be used for phase contrast imaging. The basic principles on the "method of producing an intense, high-purity K-x-ray beam" is described in U.S. Pat. No. 3,752,989 by Joseph W. Motz et al in 1973 (12). It incorporated herein by reference in its entity. It is adapted here for K-x-ray imaging combined with all field simultaneous electron or photon beam radiation therapy. To minimize the bremsstrahlung and scatter radiation reaching the stationary detectors 114 placed at the opposite side of the treatment heads, they are kept as inactive during this phase of imaging. In this instance, the imaging and treatment are done sequentially. First one side of such a treatment setup is exposed to 1-4 MeV electron beam. Its backward scattering K-x-rays is collected in that side's stationary detectors 114. The forward transmitting bremsstrahlung will reach the opposite side's stationary detectors 114 but they are kept as inactive and data from those opposite side's stationary detectors 114 is not collected during this sequential imaging process. Such imaging lasts only a few seconds. Afterwards, photon or higher energy electron all field simultaneous radiation therapy of that side of a patient is delivered. Similarly, this process of imaging with backward traveling K x-ray followed by photon or high energy electron all field simultaneous radiation of the opposite side is done. Again, first the simultaneous low energy electron beams from the other side treatment heads are activated for imaging with backward transmitting K-x-rays. These K-ray passes through the target, the patient, and then it transmits backward towards the detectors placed on that side. In the detector, it is processed by the method of time sequential data collection. After such electron beam exposure to generate K x-ray for imaging, that side's all field simultaneous photon or high energy electron beam radiation therapy is rendered. Like before, to minimize the bremsstrahlung x-rays and the scatter radiation induced image distortions, the stationary detectors 114 of the opposite side is kept as inactive. In this sequence, data is not collected from those detectors. This mode of few seconds lasting interrupted imaging and treatment of one side followed by such imaging and treatment of the opposite side has only a few seconds overall duration.

FIG. 10A shows the beam storage ring 128 from which synchronized multiple simultaneous electron and monochromatic x-ray beams are switched on for all filed simultaneous radiation therapy and imaging. The interaction of the laser photon beam with electron beam creates the inverse Compton scattering monochromatic high-flux, short-pulse x-ray. As shown in FIG. 1D, both the electron and the monochromatic x-ray beam travels together in the forward direction of the electron beam. They are then switched into the beam storage ring 128. The method of beam switching of multiple simultaneous electron beams from the beam storage ring 128 is adapted from U.S. Pat. No. 4,455,277 issued in 1984 to Schlitt L. G, "electron beam magnetic switch for a plurality of free electron lasers" (13). This patent is incorporated herein by reference in its entity. In the invention that is described here, a much different new approach is taken. In this instance, no wiggler magnets are used as in U.S. Pat. No. 4,455,277. The beam input magnets and beam output magnets are much different. The beam switching from the beam storage ring 128 is similar to those described in FIG. 3 and FIG. 4. In the above referenced U.S. Pat. No. 4,455,277, the electron beam switching magnets have 3 nsec rise time and its ring diameter is about 86 meters. By reducing the rise time of the magnet and the pulse length the diameter of the beam storage ring 128 is much reduced (13), to about 8 ft. To adapt the ring system and switching of multiple simultaneous electron beams from a single accelerator produced electron beam for all field simultaneous radiation therapy of this invention, the magnetic switch's rise time is reduced to less than 0.25 nsec. The inverse Compton scattering's collilinear x-ray and spent electron beam 14 is illustrated in FIG. 1D. In FIG. 10A these collilinear beams are numbered as 133. They are bent by the beam input magnet 130 for their injection into the beam storage ring 128. The collilinear spent electron beam and the monochromatic x-ray beam 133 are focused by quadrupole focusing magnet 15. The focused spent electron beam and monochromatic x-ray beam 133 are bent to 22.5 degree by the input magnet 130 before their switching into the beam storage ring 128. From the electron beam injection beam line 134, such bent and focused electron and x-ray beams are switched into the short diameter beam storage ring 128. The beam storage ring 128 contains fast magnetic switches having rising time of less than 0.25 nsec. It divides the electron beam pulse into a sequence of separate electron beam pulses by decomposing the electron beam into separate individual beam segments. The individual beam segments are delayed in a manner so that each beam segments are at their respective beam switching point 136 when they are switched into their respective beam transport pipe 54 shown in FIG. 10C. These beamlets are then transported to their respective therapy unit's treatment head 138 and to the imaging x-ray unit's head 140. Each beam segment's delayed arrival at beam switching point 136 is achieved by arranging each beam segments to travel in an approximate circular path in the beam storage ring 128 and adjusting the beam segment's transit time from one beam switching point 136 to the next beam switching point 136 in the beam storage ring 128 as equal to the sum of the beam segment length and the magnetic switch's rise time.

Figure 10B:
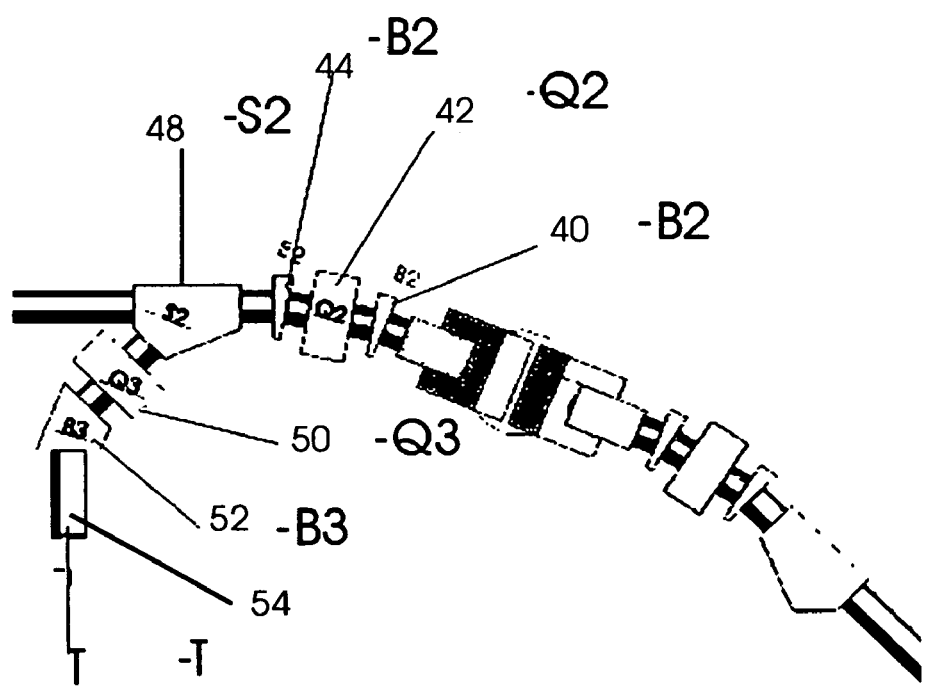
FIG. 10B: illustrates a 90 degree switching of the collilinear electron and monochromatic x-ray beams from the beam storage ring and their injection into a beam transport pipe that leads these beams towards a therapy unit's treatment head and to an imaging x-ray unit's head for radiation therapy and monochromatic x-ray imaging.

The beam is focused and steered around the beam storage ring 128 by quadrupole focusing elements 42 and the 11.25 degree bending magnets 40 shown in FIG. 10B (not shown here). When the beam storage ring 128 is filled with such beam segments, all the beam switching magnets, the 11.25 degree bending magnet 44, the 45° bending magnet 48, quadruple focusing element 50, and another 45 degree bending magnet 52 are activated. This switching of the beam is similar to such beam switching from the octagonal beam line shown in FIG. 3 and FIG. 4 but the bipolar magnet 46 shown in FIG. 3 and FIG. 4 is removed. It is shown in FIG. 10B.

In such configured all filed simultaneous radiation therapy system, eight therapy units treatment heads and eight imaging units treatment are incorporated in one embodiment for stationary eight simultaneous monochromatic x-ray beams for CT imaging and eight therapy units for simultaneous eight filed radiation therapy. This ratio of the therapy unit and imaging unit can be varied. The number of the imaging unit can be 1, 2 or 4 etc. The rest of the switched beams are then used for all field simultaneous radiation therapy, namely with 15, 14, or 12 simultaneous beams for radiation therapy with 15, 14 or 12 therapy unit heads and so on. An alternative system can be configured with more or lesser switched beams from the beam storage ring 128, namely with 32 or only 4, 6, 8 or 12 etc for therapy and imaging.

In sequential imaging mode, the segments of both electron and the monochromatic x-ray beams arriving at the beam switching points 136 in beam storage ring 128 are switched on in sequence by sequentially activating the beam switching magnets 44, 48, 50 and 52. The beams are switched from the beam storage ring 128 before the beam storage ring 128 is filled with all segments of the beams as in the case of simultaneous beams switching. It facilitates sequential switching of the monochromatic x-ray beam and directing it to the imaging x-ray unit's head 140 as described in FIG. 10B. From the imaging unit's head 140, the x-ray beam passes through the imaging target in a patient. Its attenuated monochromatic x-ray reaches the stationary detectors 114 as described before in FIG. 7 and FIG. 8. Similarly, each beamlets with monochromatic high-flux short-pulse x-ray beam segments arriving in the beam storage ring 128 is switched in sequence towards each segmented beam's imaging x-ray unit's head 140. The monochromatic high-flux short-pulse x-ray passing through the patient and its attenuated beam arriving at the stationary detectors 114 is processed in sequence, one beam at a time. It renders sequential firing of monochromatic x-ray from multiple fixed monochromatic high-flux short-pulse x-ray sources. The attenuated beam arriving at the stationary detector 114 is almost devoid of scattered radiation. This sequential switching and exposure of an imaging region in a patient with a number of monochromatic x-ray beams takes only a few nsec. The inherent superior image quality of monochromatic high-flux short-pulse x-ray (100 to 1000 times more than imaging with bremsstrahlung x-rays) is further enhanced by this method of sequential firing of multiple monochromatic high-flux short-pulse x-ray of a target in a patient. Such improved imaging quality is not feasible with polychromatic bremsstrahlung x-ray. It also has much more superior quality imaging than imaging with a single monochromatic x-ray beam that is deflected several times as described in U.S. Pat. No. 6,687,333 by Carroll et al (2).

These multiple simultaneous monochromatic high-flux short-pulse x-ray beams and electron beams facilitates radiation therapy combined with high efficiency monochromatic x-ray CT imaging as described under Methods of Operation. In HART and radiosurgical procedures with high radiation dose, such verification on the accuracy of patient set up and treatment facilitates high precision radiation therapy.

The imaging with monochromatic x-ray beam is performed with multiple simultaneous beams from a series of x-ray beamlets. The collimation with arced collimator 110 and the collimated beam guide 112 minimize the scattered beam reaching the stationary detectors 114. The image quality of monochromatic high-flux short-pulse x-ray is 100 to 1000 times more than that for bremsstrahlung x-rays. It renders superior quality imaging. It has much more superior quality imaging than imaging with a single monochromatic x-ray beam that is deflected several times as described in U.S. Pat. No. 6,687,333 by Carroll et al (2).

Iodine that is tagged to tumor specific compounds could give tumor specific, iodine k, l, m, n characteristic photon and electrons. Alternatively, implanted gold nano particles in a tumor could be used as a vehicle to generate gold specific k, l, m, n shell characteristic photon and electrons. The average kα resonant energy of gold is 68 keV (17). Exposure of gold nanoparticles implanted in the tumor with external monochromatic x-ray tuned to 68 keV k-shell binding energy of gold atom elicits gold specific Auger radiation that delivers tumor specific radiation therapy. Tuned external monochromatic x-ray of 68 keV would have penetrating power close to about 10 cm (26). It would be sufficient to treat a tumor with Auger transformation radiation from implanted gold nanoparticles into the tumor. Similar tumor specific radiation is given with tumor receptor bound iodinated steroid hormones like estrogen receptor bound iodinated estrogen.

The monochromatic x-ray generated by the interaction of electron with laser beam is not filtered with flattening filter. Hence it is a pencil beam. A pencil beam that is not filtered with a flattening filter has about more than two and a half time penetrating power than its divergent beam that is filtered through a flattening filter. The 6 and 10 MV photon beams that are not filtered through the flattening filters to make them as divergent beams have penetrating power that is equivalent to 17 and 24 MV photon (16). Hence the penetrating power of the turned 32 keV monochromatic x-ray beam could be equivalent to about the penetrating power of 90 keV x-ray. The peak emission of a 250 kVp polychromatic bremsstrahlung x-ray is about 81 keV (17). Hence it would be sufficient to reach iodinated steroid bound to steroid receptor like estrogen receptor bound iodinated estrogen in a tumor at a depth about 10 cm from the skin. External radiation with tuned 33.2 keV monochromatic x-ray to a tumor that is at several centimeters depth from the skin and has receptor bound iodinated steroid facilitates tumor specific Auger transformation radiation.

The radiological examinations with monochromatic x-rays has many applications other than its medical use. Computerized Tomography and Radiology with monochromatic high-flux short-pulse x-ray could be used for screening of explosives. It improves the image quality 100 to 1000 times more than imaging with bremsstrahlung radiation. It is used for whole body split second CT imaging to detect explosives worn under cloths. It detects the minor details of the fabrics and its composition. It also detects otherwise undetectable instruments worn for destructive purposes. This facilitates split seconds whole body screening of passengers at a busy airport. Likewise it has many industrial applications. It's very high quality imaging can detect minor fractures and defects in equipments and instruments made with precision engineering. Its use thus expands to a wide arena of innovative radiology.

FIG. 10B illustrates the 90 degree bent collilinear electron and monochromatic x-ray beam's switching from the beam storage ring 128 and their injection into a beam transport pipe 54 that leads these beams towards a therapy unit's treatment head 138 and to an imaging x-ray unit's head 140 for radiation therapy and monochromatic x-ray imaging. To switch the collilinear electron and monochromatic x-ray from the beam storage ring 128, first they are bent to 90 degrees. These beams are made to make a 45° bend with the bending magnet 48. This bent beam is then focused with the quadruple focusing element 50. The 45 degree bending magnet 52 bends these beams once again to 45 degree. This 90 degree bent collilinear electron and x-ray beams passes through a beam transport pipe towards 54. The collilinear electron and x-ray beams are switched simultaneously into the beam transport pipe 54. These beams are then separated and taken to each beamlets respective therapy unit's treatment head 138 and imaging x-ray unit's head 140 as illustrated in FIG. 10C.

Figure 10C:
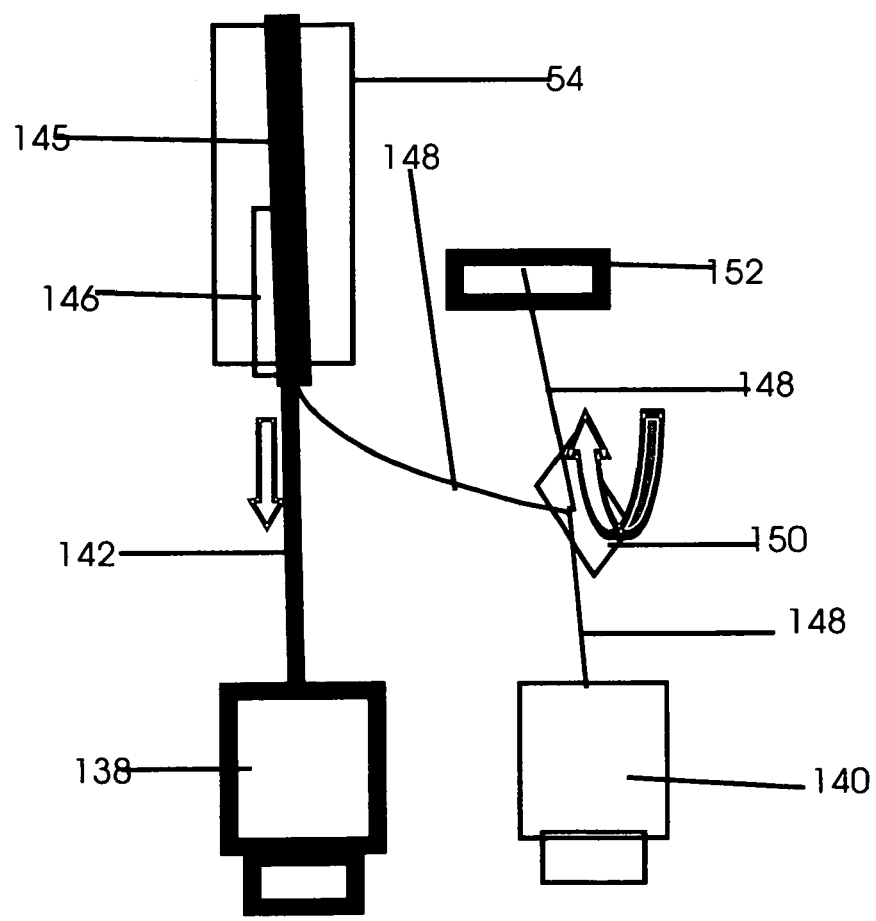
FIG. 10C: shows the collilinear electron and monochromatic x-ray beam segments switched from the beam storage ring and its traveling through the beam transport pipe, their separation into an electron beam and a monochromatic x-ray beam and their subsequent transport to a therapy unit's treatment head and to an imaging unit's treatment head.

FIG. 10C shows the collilinear electron and monochromatic x-ray beam segments 145 switched from the beam storage ring 128 and as traveling through the beam transport pipe 54, their separation into spent electron beam 142 and a monochromatic deflected x-ray beam 148 and their subsequent transport to therapy unit's treatment head 138 and to imaging unit's treatment head 140. It shows one of the many sequentially switched collilinear electron and x-ray beams switched from the beam storage ring 128. The method of beam switching from the beam storage ring 128 is shown in FIG. 10B. The switched inverse Compton scattering's electron and monochromatic x-ray beam segments 145 are shown as traveling collinearly in the forward direction (arrow) of the electron beam. The graphite mosaic crystal 146 deflects the monochromatic x-ray beam (2). The deflected x-ray beam 148 travels either towards imaging x-ray unit's head 138 or away from it by deflecting it with a rotateable x-ray deflecting mirror 150. When the rotateable x-ray deflecting mirror 150 is rotated as pointing towards the imaging x-ray unit's head 138, at 90 degree angles downwards, it is directed towards the x-ray imaging unit's head 138. The x-ray beam is absorbed by the x-ray beam absorber 152 when the rotateable deflecting mirror 150 is rotated upwards facing the beam absorber. If no simultaneous imaging and radiation therapy is not the goal but only imaging, then imaging is performed and the electron beam is absorbed by the therapy unit's treatment head's 138 closed collimators.

Figure 11A:
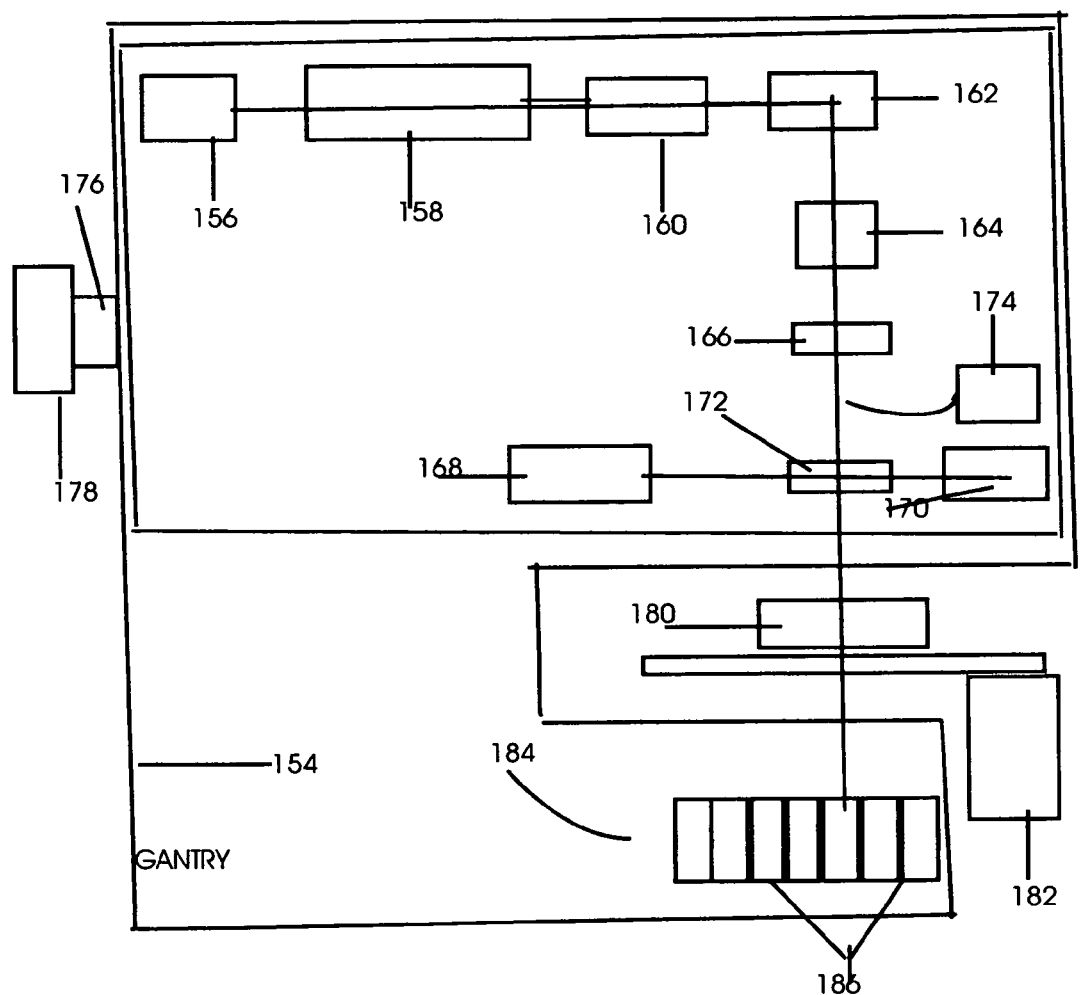
FIG. 11A: is an illustration of the gantry with an accelerator and laser beams described in U.S. Pat. No. 7,027,553 (22) which is incorporated herein in its entirety by reference

When this imaging/treatment system is not in imaging mode, the rotateable x-ray beam deflecting mirror 150 is rotated to direct the beam away from the patient, towards the x-ray beam absorber 152. When this imaging/treatment system is in radiation therapy mode, the jaws (not shown) in the therapy unit's treatment head 138 are opened to allow the photon or electron beam to pass towards the photon generating target or electron beam flattening filter and ultimately for treating the target in a patient or towards the radiation measuring equipments used for calibration of this system's radiation outputs. FIG. 11A is an illustration of the gantry with an accelerator and laser beams described in U.S. Pat. No. 7,027, 553 which is incorporated herein in its entirety by reference (22). The rotating gantry 154 contains a electron gun 156, a linear accelerator 158, a focusing element quadrupole triplet 160, an achromatic magnet 162, collimator 164, ion chamber 166, laser source-1, 168, laser source-2, 170, a mirror 172, an electron dump 174, shaft 176, motor 178, object 180, table 182, detector array 184, and detector element 186. In U.S. Pat. No. 7,027,553 (22) laser beam-1 and laser beam, -2 are shown to interact with the electron beam of energy ranging from 10-100 MeV that produce inverse Compton scattering x-ray which is used for monochromatic CT imaging. (In FIG. 2 of U.S. Pat. No. 7,027,553, the electron dump 72 is illustrated as before the inverse Compton scattering interaction of electron with two laser photon beams. It is an error. If the electron beam is deflected away before the Compton scattering interaction of electron and laser, there will not be any monochromatic x-ray generation. Hence there cannot be any CT imaging with monochromatic x-ray as is described in U.S. Pat. No. 7,027,553, (22)). By changing the wave lengths of the laser-1 and laser-2, or by changing the energy of the electron beam, the energy of the monochromatic x-ray is varied. The signaling of the laser beam and electron beam is synchronized. It is shown as before the interaction of electron and laser but it should be after the interaction of electron beam with laser beam, the electron beam is dumped as a waste product into the electron dump 174. Exposure of a target with monochromatic x-ray attenuates the x-ray. This attenuated monochromatic x-ray is collected in the detector array's 184 detector elements 186 for image processing.

Figure 11B:
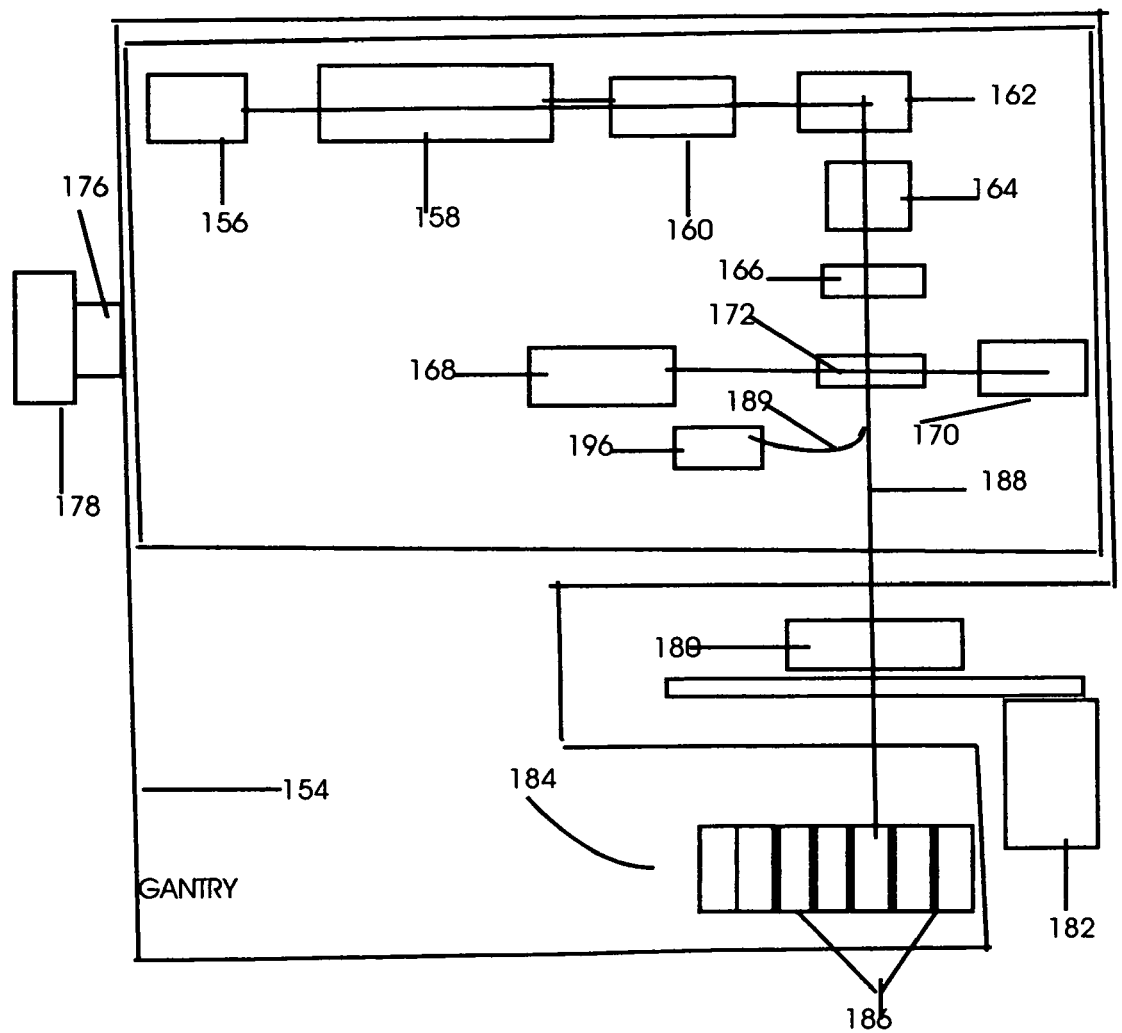
FIG. 11B: shows this invention's reuse of the spent electron beam that is dumped in U.S. Pat. No. 7,027,553.

FIG. 11B shows this invention's reuse of the spent electron beam that is dumped in U.S. Pat. No. 7,027,553. In this invention, the post Compton scattering spent electron beam 188 is not deflected away towards the electron dump 174. The monochromatic x-ray 192 is deflected away from the electron beam with graphite mosaic crystals 190 (2) as described under FIG. 1A, FIG. 1B and FIG. 1C. The deflected monochromatic x-ray beam 190 is either used for imaging as described under FIG. 10C or it is absorbed by an x-ray bam absorber 196. Thus the post Compton scattering spent electron beam 188 is not wasted, it continues its path towards the object 180 to render the radiation therapy. In this instance, the deflected monochromatic x-ray beam 192 is either absorbed by an x-ray beam absorber 196 or it is used for imaging as described under FIG. 10C. Alternatively, this monochromatic x-ray beam is used for external monochromatic x-ray radiation therapy. It is also described before. In this instance, the treatment is rendered with monochromatic x-ray combined with electron or photon beam that the post Compton scattering spent electron beam 188 generates. Alternatively, the laser beams are not activated and the electron beam alone is used for all filed simultaneous radiation therapy as described under FIG. 10C. The electron beam continues its straight path towards the object and radiates it. By varying the electron beam's energy or laser beam's wavelength, the energy of the monochromatic x-ray is varied and new varying energy spent electron beams and monochromatic x-ray beam is generated. By varying the electron beam's energy, the depth dose need to treat a tumor is also met. Higher the electron energy, deeper the 80-90 percent depth dose of the electron beam or the photon beams that it generates. If it were a radiation therapy with monochromatic x-rays, the electron beam is deflected away from the monochromatic x-ray and is dumped into the electron dump 174. The gantry is made as a rotating or as a stationary gantry. The rotating gantry facilitates imaging combined with rotational radiation therapy either as combined tumor specific tuned monochromatic x-ray along with electron or photon beam or with tuned tumor specific monochromatic x-rays or with electron or photon beam alone. Likewise, the stationary beam facilitates imaging combined with stationary beam radiation therapy either as combined tumor specific tuned monochromatic x-ray along with electron or photon beam or with tuned tumor specific monochromatic x-rays or with electron or photon beam alone. Tumor specific external monochromatic x-ray radiation therapy combined with tumor seeking heavy atom or with implanted heavy elements are described under FIG. 10A. Radiation therapy with spent electron beam is also described in FIG. 10C.

Methods of Operation

The inverse Compton scattering's multiple simultaneous monochromatic high-flux short-pulse x-ray beams or single x-ray beam facilitates high efficiency monochromatic x-ray CT imaging combined with radiation therapy. Simultaneous radiation therapy and imaging with monochromatic x-ray-CT imaging is feasible but these combined beams might cause high scatter radiation that might cause poor image quality. Hence imaging is preferred just before the radiation therapy to check the accuracy of the patient setup for radiation therapy. After the preliminary imaging, the simultaneous imaging and radiation therapy will give sufficient information on the accuracy of the delivered radiation therapy. Since it is single session or fewer session radiation therapies, such treatment accuracy verification improves the quality of the radiation therapy. In IMRT and radiosurgical procedures with high radiation dose, such verification on the accuracy is most important. It is a modified version of radiation therapy patient setup simulation and treatment. When imaging alone is performed with monochromatic x-ray, the electron beam is blocked. If the treatment head is equipped with photon generating target, it is withdrawn from the electron beam's path in the therapy unit's treatment head 138. The electron is blocked by an electron beam absorber (not shown) or by closure of primary and secondary jaws in the treatment head. The jaws absorb the electron beam without generating much contaminating radiation.

Imaging with monochromatic x-ray beam is performed as with multiple simultaneous beams from a series of x-ray beamlets or with a single beam. In simultaneous x-ray beam imaging mode, all the segments of the mostly monochromatic high-flux short-pulse x-ray beams are deflected towards the imaging target in a patient. Because of a series of cross firing simultaneous beams, more scattered x-ray might reach at the arced collimator 110 and the stationary detector 114 shown in FIG. 7 and in FIG. 8, but they are collimated with arced collimator 110 and the collimated beam guide 112. This eliminates and or reduces the scattered radiation reaching the stationary detectors 114. The inherent superior image quality of monochromatic high-flux short-pulse x-ray, 100 to 1000 times more than that for bremsstrahlung x-rays combined with the multiple simultaneous exposure with monochromatic x-ray beams that enhances the details in an image and scatter radiation filtering away from the stationary detectors 114 by the arced collimator 110 and by the collimated beam guide 112 renders much superior quality imaging. It has much more superior quality imaging than imaging with a single monochromatic x-ray beam that is deflected several times as described in U.S. Pat. No. 6,687,333 by Carroll et al (2).

In sequential imaging mode, the segments of both electron and the monochromatic x-ray beams arriving at the beam switching points 136 in beam storage ring 128 are switched on in sequence by sequentially activating the beam switching magnets 44, 46, 48, 50 and 52. The beams are switched from the beam storage ring 128 before the beam storage ring 128 is filled with all segments of the beams as in the case of simultaneous beams switching described before. It facilitates sequential switching of the monochromatic x-ray beam and directing it the imaging x-ray unit's head 140 as described in FIG. 10B. From the imaging unit's head 140, the x-ray beam passes through the imaging target in a patient. Its attenuated monochromatic x-ray reaches the stationary detectors 114 as described before in FIG. 7 and FIG. 8. Similarly, each beamlets with monochromatic high-flux short-pulse x-ray beam segments arriving in the beam storage ring 128 is switched in sequence towards each segmented beam's imaging x-ray unit's head 140. The monochromatic high-flux short-pulse x-ray passing through the patient and its attenuated beam arriving at the stationary detectors 114 is processed in sequence, one beam at a time. It renders sequential firing of monochromatic x-ray from multiple fixed monochromatic high-flux short-pulse x-ray sources. The attenuated beam arriving at the stationary detector 114 is almost devoid of scattered radiation. This sequential switching and exposure of an imaging region in a patient with a number of monochromatic x-ray beams takes only a few nsec. The inherent superior image quality of monochromatic high-flux short-pulse x-ray (100 to 1000 times more than imaging with bremsstrahlung x-rays) is further much more enhanced by this method of sequential firing of multiple monochromatic high-flux short-pulse x-ray to a target in a patient. Such improved imaging quality is not feasible with polychromatic bremsstrahlung x-ray. It also has much more superior quality imaging than imaging with a single monochromatic x-ray beam that is deflected several times as described in U.S. Pat. No. 6,687,333 by Carroll et al (2).

Screening for Concealed Elements Worn on to the Body or Contained in a Container by Whole Body Computerized Tomography and Radiology with Monochromatic High-Flux Short-Pulse X-Rays and Spent Electron Beam.

The inverse Compton scattering interaction of electron beams of varying energies with multiple laser beams of varying energies is used for differential analysis of exposure of an object with varying energy monochromatic x-rays. It detects elements of different atomic structure by their differential Auger transformation radiation and their spectrums. In a container analysis, the specific atomic spectrums of Auger transformation radiation of high and low atomic weight substances and its comparison with known Auger emission of high and low atomic weight elements detects suspect elements like uranium or elements used as explosives. It detects the minor details of the fabrics and its composition as well as if it were equipped with instruments for destructive purposes including for explosive purposes. This facilitates split seconds screening of passengers at a busy airport with much higher precision than imaging with a single energy single beam exposure with monochromatic x-ray or with bremsstrahlung x-ray. It is much more superior to imaging with varying energy bremsstrahlung x-ray and its spectral pixel analysis (27). Simultaneous monochromatic beams of varying energies and their very high quality imaging are used to analyze objects with greater clarity. It detects minor fractures and defects in equipments and instruments made with precision engineering by high quality imaging and differential pixel analysis of exposures with tuned monochromatic x-rays of varying energies.

Imaging with monochromatic high-flux short-pulse x-rays has a number of clinical imaging advantages. They are briefly summarized in U.S. Pat. No. 6,687,333 by Carroll et al (2). It facilitates much lower dose radiological examinations, 3-D volumetric monochromatic mammography, tunable k-edge radiographs and CT of different organs, brochoscopy after inhaling charcoal dust nano particle adsorbed with iodinated steroids like cortisone or estrogen (15) or with radiodense gases, tumor specific imaging and radiation therapy of tumors that posses high affinity binding to tumor seeking compounds tagged with iodine or similar elements (2).

Hyperthermia is administered for 40-60 min with readily available commercial hyperthermia machines like those employing electromagnetic and ultrasound techniques for superficial heating, hyperthermia with interstitial local heating, or with interstitial microwave antennas or radiofrequency electrode system or with interstitial ultrasound applicators or intracavitary local heating or regional and whole body heating machines. The 40 to 60 min hyperthermia is administered during simulation, conformal block making, and treatment planning. If it is combined with image guided surgery and if it will not interfere with the surgery, hyperthermia is also administered during surgical preparation of the patient. Since it is most often a single session high dose and biological dose rate radiation therapy procedure, patients are also anesthetized as may be needed. Image guided surgery is a part of this combined treatment. Hence it is convenient to administer higher temperature hyperthermia under anesthesia. For surgery, patient will be under anesthesia. The single session hyperthermia overcomes the thermotolerance associated lesser effectiveness of tumor cell kill when hyperthermia is repeated as in conventional fractionated hyperthermia.

Patient is placed on to the imaging and table 96 with minimal immobilization so that it will not interfere with the online imaging. With the patient in treatment position on the table 96, monochromatic x-ray CT imaging is done from which the treatment region is determined and the treatment plan is made. The treatment itself lasts only a few seconds during which a patient can hold the breath very easily. Hence, no complex breathing synchronized radiation therapy as is needed as in present art of breathing synchronized radiation therapy. Imaging with about 100-1000 time higher quality monochromatic x-ray-CT with much lesser eradiation dose to patient is acquired for image guided radiation therapy. Likewise, 100-1000 times high quality diagnostic monochromatic CT imaging is acquired with low radiation dose to the patient. These images are reconstructed by the image-processing computer and projected onto a 3-D stereoscopic LCD monitor as 3-D VR CT. If available, CT, MRI and PET images are fused together and projected on to the monitor. It also includes the scout views of the patient's treatment area. Multiple beams are used to render the treatment to all the treatment fields simultaneously. Their field sizes vary. Each beam is collimated with primary and secondary collimators. Multiple smaller fields within a smaller field are treated like the "step and shoot" method of treatment with MLC. However there are no MLC in this case. Individual treatment field is shaped with the field shaping tungsten powder mixture paste. Likewise, multiple smaller fields are treated simultaneously with monochromatic x-ray pencil beams as by the "step and shoot" method. Multiple smaller fields are also treated simultaneously with monochromatic x-ray pencil beams as concomitant boost treatment when monochromatic x-ray radiation therapy is combined with higher energy photon or electron. In such instances, all the treatment fields are treated simultaneously with higher energy electron or photon separately.

For tumor specific monochromatic all field simultaneous radiation therapy of breast cancer, the method of high affinity receptor bound directly iodinated estrogen is used to elicit Auger emission radiation therapy. The directly iodinated estrogen is administered intravenously. It accumulates in the estrogen receptor positive breast cancer. The iodinated estrogen binds to estrogen receptor present in the cell membrane. The iodinated estrogen thus bound to estrogen receptor is then transported into the cell interior. Alternatively, iodinated estrogen adsorbed to charcoal dust nano particles is injected directly into the tumor as an implant. The iodinated estrogen bound to tumor is then radiated with tuned monochromatic x-ray of 32 keV. Likewise, iodinated androgen is used to radiate the prostate cancer either by its intravenous injection or by its direct implant as nano particle charcoal bound iodinated testosterone. The K-shell electron binding energy for iodine is 32 keV. The tuned external monochromatic x-ray beam is generated by the inverse Compton scattering of electron and laser beams. This collilinear electron and laser beams are made to circulate in the beam switching ring 128 or in the octagonal beam line 66. This beam is then bent towards the target as described in FIG. 3 and in FIG. 4. The interaction of the monochromatic x-ray tuned to 32.2 keV x-ray with iodine's k, l, m, n-shells elicits iodine specific Auger emission. With tumor bound or implanted iodine, it renders tumor specific local radiation. It induces disruption of the tumor cell's DNA single and double stands which leads to tumor specific radiation that cause tumor specific cell kill.

Iodine that is tagged to tumor specific compounds could give tumor specific, iodine k, l, m, n characteristic photon and electrons. Alternatively, implanted gold nano particles in a tumor could be used as a vehicle to generate gold specific k, l, m, n shell characteristic photon and electrons. The average ka resonant energy of gold is 68 keV (17). In this instance, the incident monochromatic x-ray that is tuned to 68 keV of gold atom's k, l, m, n shell binding energies Auger cascade radiation within the tumor, tumor specific radiation therapy. Such tuned monochromatic x-ray would have penetrating power about 10 cm (26). Such radiation therapy with monochromatic x-ray is used alone to treat a tumor or as concomitant boost for treating a tumor with higher energy photon or electron. In the later case, before or after treating a tumor with higher energy photon or electron, the tumor specific k, l, m, n characteristic photon and electron radiation is delivered.

Alternatively, implanted gold Nanoparticles into the tumor are radiated with tuned monochromatic x-ray of 66 keV. The K-shell binding energy of gold is 66 keV. The interaction of this tuned monochromatic 66 keV x-ray with gold k-shell elicits gold k-shell specific Auger emission. It radiates the tumor cell specifically. It induces tumor cell's single and double stand DNA breaks leading to tumor specific radiation and tumor specific cell kill. The pencil beam characteristics of monochromatic x-ray render sufficient penetration to treat a deep seated tumor.

The monochromatic x-ray generated by the interaction of electron with laser beam is not filtered with flattening filter. Hence it is a pencil beam. A pencil beam that is not filtered with a flattening filter has about more than two and a half time penetrating power than its divergent beam that is filtered through a flattening filter. The 6 and 10 MV photon beams that are not filtered through the flattening filters to make them as divergent beams have penetrating power that is equivalent to 17 and 24 MV photon (16). Hence the penetrating power of 33.2 keV monochromatic x-ray beam could be equivalent to about the penetrating power of 90 keV x-ray. The peak emission of a 250 kVp polychromatic bremsstrahlung x-ray is about 81 keV (17). A tuned 33.2 keV monochromatic x-ray displaces the electron from the k-shell. It renders emission of characteristic photon or Auger electron (23). The total energy of characteristic photon from k, l, m and n shells in iodine is 33.2 keV. Such Auger resonance releases very large amount of localized x-ray and electron emission (24). The depth dose of 10 cm is obtained from gold particle's Auger transformation induced mostly monochromatic x-rays (26).

When the radiation therapy is combined high energy spent electron generated photon or electron and with monochromatic x-ray radiation, they are rendered together or separately.

If the radiation therapy mode is the combined with high energy electron and monochromatic x-ray radiation, the radiation with higher energy electron is rendered separately or combined with monochromatic x-ray radiation. The electron energy is elected from a group of multiple electron energy options to suit the tumor depth. In the separate mode of radiation with electron beam only the electron-laser inverse Compton scattering is suppressed as shown in FIG. 1C. The electron beam is transported into the octagonal beam line 66 or to the beam storage ring 128. The switched electron beam from the octagonal beam line 66 or from the beam storage ring 128 is then directed to the target with an electron cone as in conventional electron beam treatment of a tumor. The electron energy is elected to suit full coverage of the tumor by 90 or 80 percent line of the depth dose of the electron beam. The advantages of the electron beam radiation includes that it renders no exit dose to the opposite side of the beam entry. After treating a tumor with such separate electron energy, tumor specific monochromatic radiation is delivered. In this case, it is like a concomitant boost radiation therapy.

When the high energy photon or electron radiation is combined with radiation therapy with monochromatic x-ray, the spent electron beam after the inverse Compton reaction is reused. In this instance, after the interaction of electron and the laser beam that generates the monochromatic high flux short wave x-ray, the spent electron beam is not dumped away as a waste product. Instead, the spent electron beam is diverted for electron beam radiation therapy or to generate photon beam. It is described in FIG. 10A.

The method of imaging when the treatment is rendered with various modalities of treatment described in this invention is described before under FIG. 7 and FIG. 8. When monochromatic x-ray beam is the mode for imaging the suitable detectors are elected from the group described under FIG. 7. The detectors are selected from the group of scintillation based detectors, photon counting detectors or energy discriminating detectors.

Each of the treatment head's accessory holders 4 is equipped with the block-forming tray. The beam blocking tungsten powder mixture is made into a thick paste by mixing it with resin that acts like a binder. Methods of such tungsten powder block making are described in previous U.S. Provisional Patent Application 60/790,192, filed on Apr. 6, 2006 and its regular patent application Ser. No. 11/974,876 filed on Apr. 5, 2007 (21). Multiple beams from varying angles are used for simultaneous treatment of all the treatment fields. Each of the treatment fields is simulated and its shaped field block is made to make the beam to pass through the opening in the block in conformity with the geometry of the tumor region treated from that field. The filed shaping blocks for monochromatic x-ray and for electron is much simpler, they do not need heavy, increased thickness blocks. They are made of simple lead-cuts or simpler Cerrobend blocks that are commonly used in radiation therapy. The radiation oncologist works like a surgeon and a sculptor to shape each of the treatment field's blocks that fits with the tumor volume and its margins so that it fits tightly like tailor-made attire to do the tight fitting conformal radiation therapy.

After such block making, repeat monochromatic x-ray CT is taken to check the conformal filed setup that encompasses the entire tumor volume with desired margins. Those images are projected on to the stereotactic 3-D monitor and to 2-D monitor to check the field setups and the beams full coverage of the tumor. If it is found to be satisfactory, it is used for the treatment planning. If further adjustments in block's opening are needed, then the necessary such adjustments are made as describe above before proceeding to take the planning CT. Such images are stored in the treatment-planning computer for 3-D conformal intensity modulated radiation therapy planning. The treatment planning is done by the Monte Carlo method of dose calculation with advanced computing system that can complete the treatment planning and calculations in about a minute. Such combined treatment planning and dose calculation further improves the quality of the treatment.

Like in the present image guided radiation therapy, the treatment-planning computer reconstructs the 2-D images to 3-D images and its segmentations for the treatment planning. Its 3-D VR format is used for treatment planning and dose calculations. Live interactive surface and internal anatomy of the treatment site is projected as 3D-VR-image format with superimposed isodose curves onto the stereoscopic monitor and as 3-D beam's eye view onto the 2-D monitor. Live interactive necessary adjustments are made to the beam's energy, dose rate and weights with the patient in treatment position and ready to be treated. The advanced treatment planning computing system calculates the dose distribution using the Monte Carlo methods of dose calculation in about a minute.

The intensity modulation of the simultaneous beams for multiple simultaneous beams IMRT is done by selection of pencil or divergent beams and their desired energy. Variable energy electron beams circulating in the electron ring storage ring are available in this invention. It facilitates availability of variable energy photon and electron beams. Photon is generated from spent electron in the therapy unit's head 138. There are multiple variable wave length laser beams that react with electron beam. By changing the electron beam energy or the wavelength of the laser or both, the energy of the monochromatic x-ray is tuned to a desired energy for the treatment. It facilitates variable energy monochromatic x-rays and variable energy electrons and or photon beams. There are a number of simultaneous beams. By changing the energies of these beams, variable energy intensity modulated radiation therapy is rendered.

The computer generated treatment plan defines field size, the beam weight for each of the beam, pencil or divergent beam and other treatment parameters. Additional beam's intensity modulation is achieved by simple insertion of computer calculated width and thickness beam filtering materials that also compensates for missing tissue, inhomogeneity and the curvature of the treatment field on the patient etc.

REFERENCES

1. SAHADEVAN V.: Non-provisional application Ser. No. 11/998,063 filed on Nov. 27, 2007 and its provisional application 60/872,117 of Nov. 30, 2006; "Lethal and Sub-lethal Damage Repair Inhibiting Image Guided Simultaneous All Field Divergent and Pencil Beam Photon and Electron Radiation Therapy and Radiosurgery"
2. CARROLL F. E. System and Method for Producing Pulsed Monochromatic X-rays: Carroll F. E, Traeger R. H, Mendenhall, M. H, Waters J. W, Edwards, G. and Brau, C. A., U.S. Pat. No. 6,687,333 B2, Feb. 3, 2004,
3. KAERTNER F. X., Compact, High Flux, Short-Pulse X-Ray Source: Kaertner, F. X., Graves W. S., Moncton D. E. and Ilday, F. O U.S. Pat. No. 7,391,850 B2, Jun. 24, 2008,
4-1 HALL E. J., Hyperthermia, Cellular Response to Heat, in Radiobiology for the Radiologist, Hall E. J. (Ed) fifth ed., P 497-499, Lippencott Williams & Wilkins, 2000, Philadelphia
4-2 HALL E. J., Hyperthermia, The Interaction Between Heat and Radiation, in Radiobiology for the Radiologist, Hall E. J. (Ed)., p 508-510, fifth ed. Lippencott Williams & Wilkins, 2000, Philadelphia 4-3 HALL E. J., Hyperthermia, Heat and Chemotherapeutic Agents in Radiobiology for the Radiologist, Hall E. J. (Ed)., p 510-512, fifth ed. Lippencott Williams & Wilkins, 2000, Philadelphia
5. KHAN F. M.: Electron Beam Therapy, X-Ray Contamination, in the Physics of Radiation Therapy, p 317-318 Khan, F. M. (ed), 2003, Lippencott Williams & Wilkins, Philadelphia
6. KHAN F. M.: Electron Beam Therapy, Beam Collimation, in the Physics of Radiation Therapy, p 312 Khan, F. M. (ed), 2003, Lippencott Williams & Wilkins, Philadelphia
7. KHAN F. M.: Electron Beam Therapy, Problems of Adjacent Fields, in the Physics of Radiation Therapy, p 328-329 Khan, F. M. (ed), 2003, Lippencott Williams & Wilkins, Philadelphia
8. KHAN F. M.: Electron Beam Therapy, Effects of Blocking on Dose Rate, in the Physics of Radiation Therapy, p 332-333, Khan, F. M. (ed), 2003, Lippencott Williams & Wilkins, Philadelphia
9. KHAN F. M.: Electron Beam Therapy, Electron Arc Therapy, in the Physics of Radiation Therapy, p 337 Khan, F. M. (ed), 2003, Lippencott Williams & Wilkins, Philadelphia
10. KHAN F. M.: Electron Beam Therapy, Measurement of Transmission Curves, in the Physics of Radiation Therapy, p 331-332 Khan, F. M. (ed), 2003, Lippencott Williams & Wilkins, Philadelphia
11. KHAN F. M.: Electron Beam Therapy, Characteristics of Clinical Electron Beams, in the Physics of Radiation Therapy, p 307 Khan, F. M. (ed), 2003, Lippencott Williams & Wilkins, Philadelphia
12. MOTZ J. W., Method of Producing an Intense, High Purity K X-ray Beam, Motz J. W., Dick C. E., Placious R. C, Sparrow J. H., U.S. Pat. No. 3,752,988, Aug. 14, 1973
13. SCHLITZ G. L., Electron Beam Magnetic Switch for a Plurality of Free Electron Lasers, U.S. Pat. No. 4,455,277, Jun. 19, 1984
14. ENE P. M., Scatter Control System and Method for Computed Tomography, Edie P. M., De Man B. K. B., Vermlyea M. E., et al, U.S. Pat. No. 7,366,279, Apr. 29, 2008.
15. SAHADEVAN. V., Preparation of Directly Iodinated Steroid Hormones and Related Compounds, U.S. Pat. No. 4,321,208, Mar. 23, 1982
16. NUNAN C. S., X-ray and Electron Radiotherapy Clinical Treatment Machine; Patent U.S. Pat. No. 4,726,046, Feb. 16, 1988.
17. PRADHAN A. K. et al., Resonant X-ray Enhancement of the Auger Effect in High-Z Atoms, Molecules, and Nanoparticles: Potential Biomedical Applications: J. Phys. Chem. A 2009, 113, 12356-12363
18. HALL E. J., Carcinogenesis: The Human Experience, in Radiobiology for the Radiologist, Hall E. J. (Ed) fifth ed. P 145-149, Lippencott Williams & Wilkins, 2000, Philadelphia
19. SMITH-BINDMAN, et. al., Radiation Dose Associated With Common Computed Tomography Examinations and the Associated Lifetime Attributable Risk of Cancer: Arch Intern Med/Vol 169, (No 22) Dec. 14/28, 2009, p 2078-2079, 2082-2083
20. XIAOWEI YANG et al., Synergistic Activation of Functional Estrogen Receptor (ER)-α by DNA Methyltransferase and Histone Deacetylase Inhibition in Human ER-α-negative Breast Cancer Cells1, Cancer Research 61, 7025-7029, Oct. 1, 2001
21. SAHADEVAN. V., Non-provisional patent application 11,974,876 filed on Apr. 5, 2007 and its provisional patent application 60/790,192 filed on Apr. 6, 2006; "Multiple Medical Accelerators and kV-CT Incorporated Radiation Therapy Device and Semi-Automated Custom Reshapeable Blocks for All Field Synchronous Image Guided 3-D Conformal-Intensity Modulated Radiation Therapy"
22. DUNHAM B. M., Systems and Methods for Generating Images by Using Monochromatic X-Rays: Patent U.S. Pat. No. 7,027,553, Apr. 11, 2006.
23. KHAN F. M.: Characteristic X-rays, in the Physics of Radiation Therapy, p 34-35 Khan, F. M. (ed), 2003, Lippencott Williams & Wilkins, Philadelphia
24. CARROLL F. E., System and Method for Monochromatic X-ray Beam Therapy: U.S. Pat. No. 7,486,984, Feb. 3, 2009.
25. SAHADEVAN V. and SAHADEVAN V. C., Estrogen Contents of Estrogen Receptor Positive and Negative Breast Cancer: Unpublished data, 1980
26. MONTENEGRO M. ET EL., Monte Carlo Simulation and Atomic Calculations for Auger Process in Biomedical Nanotheranostics: J. Phys. Chem., A 2009, 113, 12364
27. BJORKHOLM, P., Dual Energy Radiation Scanning of an Object: U.S. Pat. No. 7,636,417, Dec. 22, 2009.
28. HALL E. J., Linear Energy Transfer: in Radiobiology for the Radiologist, Hall E. J. (Ed)., p 113-114, fifth ed. Lippencott Williams & Wilkins, 2000, Philadelphia
29. KHAN F. M.: Treatment Planning I: Isodose Distributions, B. Rotation Therapy, Example, in the Physics of Radiation Therapy, p 216-217 Khan, F. M. (ed), 2003, Lippencott Williams & Wilkins, Philadelphia

What is claimed is:

1. A system for generating multiple simultaneous tunable mostly monochromatic x-ray beams for imaging, tumor specific radiation therapy, comparative imaging and image pixel analysis of an object exposed with multiple beams of varying energies and said system's spent electron beam generating X-ray for image guided all field simultaneous radiation therapy and whole body and container imaging and said system comprising:

an electron linear accelerator generating a plurality of electron beams having multiple tunable energies;
a plurality of laser beams having varying wave lengths interacting with the plurality of electron beams to generate a plurality of tunable monochromatic x-rays of variable energies;
a short diameter circular or octagonal beam storage ring, which stores said electron beams and said generated tunable monochromatic x-rays;
a switch which simultaneously switches a duration of the generated monochromatic x-rays to picoseconds in time;
the plurality of tunable monochromatic x-rays are directed towards a plurality of treatment heads;
the plurality of tunable monochromatic x-rays are simultaneously irradiated from the treatment heads to an object at different angles for imaging and radiation therapy;
a plurality of stationary collimated detectors, which receive the plurality of tunable monochromatic x-rays irradiated from different angles, that are attenuated by the object;
imaging the object with the simultaneously attenuated monochromatic x-rays
detected by the plurality of stationary collimated detectors; and performing image pixel analysis.

2. A system for image guided all field simultaneous radiation therapy as in claim 1, where multiple simultaneous laser beams of varying wave lengths from different angels interacts with accelerated electron beam to generate inverse Compton scattering and multiple simultaneous tunable energy monochromatic x-rays.

3. A system for image guided all field simultaneous radiation therapy as in claim 1, where tunable energies multiple simultaneous photon and electron beams generated from spent electron beams of inverse Compton scattering interaction of electron and laser beams.

4. A system for image guided all field simultaneous radiation therapy as in claim 1, further consisting of tunable energies multiple simultaneous monochromatic x-rays generated from inverse Compton scattering interaction of electron and varying wavelengths laser beams.

5. A system for image guided all field simultaneous radiation therapy as in claim 1, where tunable energies multiple simultaneous monochromatic x-rays generated from inverse Compton scattering interaction of laser beams and varying energy electron beams.

6. A system for generating multiple simultaneous tunable monochromatic x-rays as in claim 1, where a plurality of segments of electron beam and its collilinear monochromatic x-ray beam are steered within a common circular beam storage ring equipped with bending and collimating magnets, electron beam segment deflecting magnets for simultaneous switching of collilinear electron and x-ray beam segments from the beam storage ring into separate beam line pipes leading to therapy unit's treatment heads and to imaging x-ray unit's heads for image guided all filed simultaneous radiation therapy and imaging.

7. A system for generating multiple simultaneous tunable monochromatic x-rays as in claim 6, wherein tumor specific radiation therapy and screening for concealed elements worn on to the body or contained in a container is with spent electron beam or photon generated from spent electron beam or with monochromatic x-ray tuned to tissue bound element's atom specific k, l, m, n shell binding energies and its Auger transformation radiation.

8. A system for generating multiple simultaneous tunable monochromatic x-rays for imaging and tumor specific radiation therapy as in claim 7, where an external monochromatic x-ray beam is tuned to the k-shell electron binding energy of a tumor seeking element's atom or a nano particle element that is implanted into the tumor to generate locally propagating characteristic photon and Auger electrons radiation that is confined within the tumor for tumor specific radiation therapy.

9. A system for generating multiple simultaneous tunable monochromatic x-rays for imaging and tumor specific radiation therapy as in claim 8, where an external monochromatic x-ray beam is tuned to 33.2 keV to elicit iodine specific characteristic photon and Auger electrons from iodinated steroid molecules that is bound to steroid receptors of the cell like estrogen receptor bound iodinated estrogen in breast cancer and testosterone receptor bound iodinated testosterone in prostate cancer.

10. A system for generating multiple simultaneous tunable monochromatic x-rays for imaging and tumor specific radiation therapy as in claim 7, further consisting of external monochromatic x-ray beam tuned to 10 to 200 keV for imaging with mostly monochromatic x-rays to minimize increased incidence of cancer from radiological examinations with polychromatic bremsstrahlung x-rays like those with computerized tomography.

11. A system for image guided all field simultaneous radiation therapy and detection of canceled objects as in claim 1, further consisting of imaging with multiple simultaneous monochromatic x-ray computerized tomography is by simultaneous switching of picoseconds duration beamlets from a beam storage ring.

12. A system for generating multiple simultaneous tunable monochromatic x-rays as in claim 1, further consisting of multiple simultaneous beams' additive high dose rate radiation therapy, imaging and detection of concealed elements in a person or in a container with inverse Compton scattering x-rays.

13. A system for generating multiple simultaneous tunable monochromatic x-rays as in claim 1, where spent electron beam of inverse Compton interaction with electron and laser switched into two beams and steered through two octagonal beam lines and to multiple treatment heads and their beams converging at the isocenter simultaneously with isocentric additive high dose rate ranging from 1,000 to 4,000 cGy per minute for high dose rate radiation therapy with lesser toxicity to normal tissue.

14. A system for generating multiple simultaneous tunable photon beams by reusing the spent electron beam of inverse Compton scattering electron-laser interaction as in claim 13, further consisting of imaging and tumor specific intensity modulated radiation therapy with varying beam intensities of each converging beams at the isocenter.

15. A system for isocentric high additive dose rate radiation therapy as in claim 13, further consisting of lesser normal tissue toxic radiation therapy combined with hyperthermia and chemotherapy to treat cancerous tumors including radioresistant and multiple times recurrent tumors that are otherwise untreatable with conventional radiation therapy.

16. A system for generating multiple simultaneous tunable monochromatic x-rays as in claim 1, where simultaneous X-ray beam generated in multiple treatment heads arranged in a circle to treat a patient with multiple simultaneous beams and for imaging combined with pixel analysis with their attenuated beam passing through image processing detectors.

17. An image processing system as in claim 16, where attenuated photon exposing the parallel opposed collimated detectors placed proximally to treatment heads.

18. A system for generating multiple simultaneous tunable photon and electron beams as in claim 1, where radiation therapy is administered with high energy multiple simultaneous electron beams with their additive high dose and dose rate at the isocenter.

19. A system for generating multiple simultaneous tunable photon and electron beams as in claim 18, further consisting of radiation therapy with electron beam segments and imaging with its tail end photon beam exiting at its opposite side and reaching the opposing stationary detectors placed proximal to treatment heads in a circle and exposing said collimated detectors with said exiting photon beams for image processing.

* * * * *